United States Patent [19]
Hasegawa et al.

[11] Patent Number: 5,512,673
[45] Date of Patent: Apr. 30, 1996

[54] PHYSIOLOGICALLY ACTIVE SUBSTANCES OF PLANT, PROCESS FOR THE PREPARATION THEREOF, AND UTILITIES THEREOF

[75] Inventors: Koji Hasegawa; Hideo Kakuta; Junya Mizutani, all of Sapporo, Japan

[73] Assignee: Research Development Corporation of Japan, Tokyo, Japan

[21] Appl. No.: 316,350

[22] Filed: Sep. 30, 1994

Related U.S. Application Data

[62] Division of Ser. No. 30,732, Mar. 12, 1993, Pat. No. 5,455,345.

[30] Foreign Application Priority Data

| May 22, 1992 | [JP] | Japan | 4-131050 |
| Sep. 16, 1992 | [JP] | Japan | 4-246813 |
| Nov. 30, 1992 | [JP] | Japan | 4-320898 |
| Feb. 26, 1993 | [JP] | Japan | 5-62729 |

[51] Int. Cl.$^6$ ............... C07H 1/08; C07H 3/04
[52] U.S. Cl. ............. 536/128; 536/123.13; 536/124; 536/4.1; 504/292
[58] Field of Search ............ 504/292; 536/123.13, 536/128, 124, 4.1

[56] References Cited

U.S. PATENT DOCUMENTS

| 3,567,421 | 3/1971 | Pape et al. | 536/21 |
| 4,774,231 | 9/1988 | Petitou et al. | 504/146 |

OTHER PUBLICATIONS

Ray et al., "Composition of Root Mucilage Polyaccharides from Lepidium Sativum," J. Exp. Bot. 39 (206) 1249–61 (1988).
Hasegawa et al., "Isolation and Identification of Lepidimoide, a New . . . ", Plant Phys. 100(2):1059–1061 (Oct. 1992).
Bajpai et al., "Structure of *Hibiscus ficulneus* Mucilage," Indian J. Chem. 7(8):780–83 (Aug. 1969).
Tomoda et al., "Plant Mucilages, XXIII. Partial Hydrolysis of . . . " Chem. Pharm. Bull., 27(7):1651–56 (Jul. 1979).
Ciuffreda et al., "An Efficient Synthesis of the . . . ", J. Carb. Chem. 8(5):805–811 (1989).
H. Molisch: "Der Einfluss einer Pflanze auf die andere Allelopathie," Gustav Fischer Verlag, Jena, 1937.
E. L. Rice (1984): Allelopathic effects of crop plants on other crops . . . , "Allelopathy" 2nd ed. pp. 41–67, Academic Press, Inc.
"Allelopathy of Cress Germinated Seeds and Tomato Seedlings," K. Hasegawa et al., Zasso Kenkyu (Weed Research, Japan), vol. 37, No. 1, 1992, Tokyo, Japan, pp. 68–71.
"Allelochemicals and Microbial Substances Produced from Cress Seedlings," K. Hasegawa et al., Zasso Kenkyu (Weed Research, Japan), vol. 37, No. 1, 1992, Tokyo, Japan, pp. 71–73.
"Allelopathy of Barnyardgrass," K. Hasegawa et al., Zasso Kenkyu, (Weed Research, Japan), vol. 37, No. 2, 1992, Tokyo, Japan, pp. 146–152.
"An Efficient Synthesis of the alpha–D–glucopyranosyl–(1–2)–alpha–L–rhamnopyranoside Unit," F. Ronchettif et al., J. Carbohydr. Chem., vol. 8, No. 5, 1989, pp. 805–811.
"Isolation and Identification of Lepidimoide, a New Allelopathic Substance from Mucilage of Germinated Cress Seeds," K. Hasegawa et al, Plant Physiol. vol. 100, 1992, pp. 1059–1061.
"Bean Sprout Rooting Inhibition by Benzoic Acid Containing Compositions," Ling Yun, Chemical Abstracts, vol. 113, 1990, Columbia, Ohio, 1990 Abstract No. 57783p.
Patent Abstract of Japan, vol. 007, No. 007 (C–144) 12 Jan., 1983, (JP–A–57 165 30 to J. Iwamura, dated 12 Oct. 1982).
Communication from European Patent Office with attached European Search Report dated 8 Oct. 1993.
"Synthesis of Ethyl and Phenyl 1–Thio–1,2–trans–D–Glycopyranosides from the Corresponding Per–O–acetylated Glycopyranoses having a 1,2–trans–Configuration using Anhydrous Ferric Chloride as a Promoter," F. Dasgupta et al., Acta Chemica Scandianavica 43 (1989) pp. 471–475.
"Use of the methylsulfenyl cation as an activator for glycosylation reaction with alkyl (aryl) 1–thioglycopyranosides: synthesis of methyl O–(2–acetaimdo–2–deoxy–β–D–glucopyranosyl)–(1→2)–α–D–glucopyranoside, a derivative of the core trisaccharide of *E, coli* K12\*," F. Dasgupta et al., Carbohydrate Research, 202 (1990) Elsevier Science Publishers B.V., Amsterdam, pp. 225–238.

*Primary Examiner*—John W. Rollins
*Assistant Examiner*—Francisco C. Prats
*Attorney, Agent, or Firm*—Finnegan, Henderson, Farabow, Garrett & Dunner

[57] ABSTRACT

The present invention relates to compounds represented by the following formula (I)

(wherein $R^1$, $R^2$, $R^3$, $R^4$, and $R^5$ independently represent a hydrogen atom or an acetyl or benzyl group, $R^6$ represents a hydrogen atom, a hydroxyl, acetoxy, or benzyloxy group, $R^7$ represents a hydrogen atom, or $R^6$ and $R^7$ together my represent another direct bond, and $R^8$ represents a carboxyl, methoxycarbonyl, hydroxymethyl, or acetoxymethyl group) or salts thereof and a process for the preparation thereof, as well as their utilities in a method for culture, a method for the growth inhibition of moyashi roots, and a method for the growth promotion of moyashi hypocotyls.

2 Claims, 21 Drawing Sheets

A. AMARANTHUS CAUDATUS L.
B. LETTUCE
C. PERSIAN SPEEDWELL
D. TIMOTHY

PHYSIOLOGICALLY ACTIVE SUBSTANCES OF PLANT, PROCESS FOR THE PREPARATION THEREOF, AND UTILITIES THEREOF

This is a division of application of Ser. No. 08/030,732, filed Mar. 12, 1993 now U.S. Pat. No. 5,455,345.

INTRODUCTION

The present invention relates to physiologically active substances of plant with a novel structure being useful for the growth regulation of agricultural products etc., a process for the preparation thereof, and utilities thereof.

BACKGROUND OF THE INVENTION

At present, "allelopathy", which is represented by the phenomenon of promotion of ripening fruits by ethylene released from other ripened fruits, is known and observed in every plant including microorganisms. Nowadays, such a phenomenon is attempted to be applied positively to the growth regulation of plants (H. Molisch: "Der Einfluss einer Pflanze auf die andere Allelopathie", Gustav Fischer Verlag, Jena. 1937), and is practically applied in some cases (E. L. Rice (1984): Allelopathic effects of crop plants on other crop plants. In "Allelopathy" 2nd ed. pp. 41–67, Academic press, Inc.).

As "allelopathy", it was found that if specific kinds of seeds or seedlings are cultured in the presence of cress plant seeds in a Petri dish, then the growth of hypocotyls is promoted, whereas the growth of seedling roots is inhibited (Zasso Kenkyu, 37, 68 (1992); Zasso Kenkyu, 37, 71 (1992).

However, the substantiality of substance bringing about such "allelopathy" has still not been identified.

"Hydroponics", i.e. a method of growing plants in an aqueous solution with nutrients dissolved, was carried out widely as "water culture" in the old days, and has become a method more frequently adopted owing to the development in plant biotechnology in recent years.

The most important item for carrying out hydroponics is to select a suitable composition to be used for a culture solution.

Typical examples of such culture solutions are Sachs' solution, Knop's solution, Hoagland's solution, etc.

Under the circumstances, the development of hydroponics using a new culture solution has been desired with the aim of establishing more efficient hydroponics.

Bean sprouts, barley malt, etc., are mainly grown legume sprouts in the dark (referred to as "moyashi", hereinafter) and 1 week or so is required for their industrial production. In recent years, it has been conducted to inhibit the growth of roots and remove roots mechanically in the production of moyashi in order to improve their value as commercial products.

It has therefore been desired to develop a method for producing moyashi of enhanced value as a commercial product in higher productivity.

In order to solve the above problem, the present inventors have isolated and identified, from seedlings of cress etc., physiologically active substances bringing about "allelopathy", have succeeded in the synthesis of said substances and derivatives thereof, and have established a new culture method comprising use of a new artificial soil or culture solution, and they have found that said substances can promote the growth of moyashi simultaneously with the growth inhibition of roots, thereby arriving at the completion of the present invention.

SUMMARY OF THE INVENTION

The present invention comprises the following inventions.

1. Compounds represented by the following formula (I):

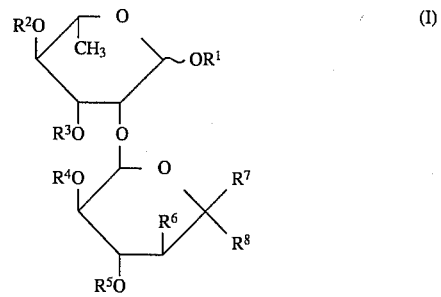

wherein $R^1$, $R^2$, $R^3$, $R^4$, and $R^5$ independently represent a hydrogen atom, or an acetyl or benzyl group, $R^6$ represents a hydrogen atom, a hydroxyl, acetoxy, or benzyloxy group, $R^7$ represents a hydrogen atom, or $R^6$ and $R^7$ together may represent another direct bond, and $R^8$ represents a carboxyl, methoxycarbonyl, hydroxymethyl, or acetoxymethyl group, and salts thereof.

2. Compound represented by the following formula (Ia):

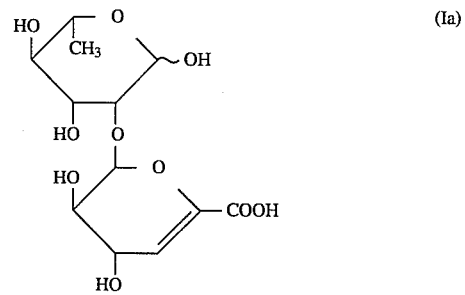

and salts thereof.

3. Compounds represented by the following formula (Ib):

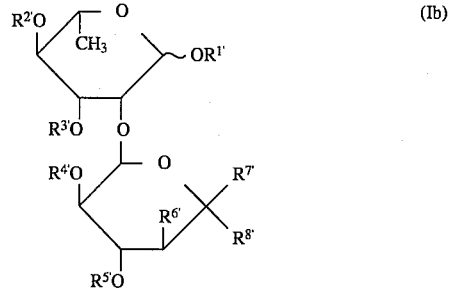

wherein $R^{1'}$, $R^{2'}$, $R^{3'}$, $R^{4'}$, and $R^{5'}$ independently represent a hydrogen atom, or an acetyl or benzyl group, $R^{6'}$ represents a hydrogen atom, a hydroxyl, acetoxy, or benzyloxy group, $R^{7'}$ represents a hydrogen atom, or $R^{6'}$ and $R^{7'}$ together may represent another direct bond, $R^{8'}$ represents a carboxyl, methoxycarbonyl, hydroxymethyl, or acetoxymethyl group, in which, if $R^{1'}$, $R^{2'}$, $R^{3'}$, $R^{4'}$, and $R^{5'}$ each represent a hydrogen atom, and $R^{8'}$ represents a carboxyl group, then $R^{6'}$ represents a hydrogen atom, a hydroxyl, acetoxy, or benzyloxy group and $R^{7'}$ represents a hydrogen atom, and salts thereof. 4. Compounds as defined in claim 1, wherein $R^1$, $R^2$, $R^3$, $R^4$, and $R^5$ each represent a hydrogen atom, $R^6$ represents a hydroxyl group, $R^7$ represents a hydrogen atom, and $R^8$ represents a carboxyl group, and salts thereof.

5. Compounds as defined in claim 1, wherein $R^1$, $R^2$, $R^3$, $R^4$, and $R^5$ each represent a hydrogen atom, $R^6$ represents a hydroxyl group. $R^7$ represents a hydrogen atom, and $R^8$ represents a methoxycarbonyl group.

6. Compounds as defined in claim 1, wherein $R^1$, $R^2$, $R^3$, $R^4$, and $R^5$ each represent a hydrogen atom, $R^6$ represents a hydroxyl group, $R^7$ represents a hydrogen atom, and $R^8$ represents a hydroxymethyl group.

7. Compounds as defined in claim 1, wherein $R^1$, $R^2$, $R^3$, $R^4$, and $R^5$ each represent a hydrogen atom. $R^6$ represents a hydrogen atom, $R^7$ represents a hydrogen atom, and $R^8$ represents a carboxyl group, and salts thereof.

8. Compounds as defined in claim 1, wherein $R^1$, $R^2$, $R^3$, $R^4$, and $R^5$ each represent a benzyl group, $R^6$ represents a benzyloxy group, $R^7$ represents a hydrogen atom, and $R^8$ represents an acetoxymethyl group.

9. Compounds as defined in claim 1, wherein $R^1$, $R^2$, $R^3$, $R^4$, and $R^5$ each represent an acetyl group, $R^6$ and $R^7$ together may represent another direct bond, and $R^8$ represents a methoxycarbonyl group.

10. A process for the preparation of the compound as defined in claim 2 or salts thereof, which comprises hydrolysis of the compound as defined in claim 9.

11. A process for the preparation of physiologically active substances of plant, which comprises immersing plant seeds in water and then collecting from the extract the compound represented by formula (Ia):

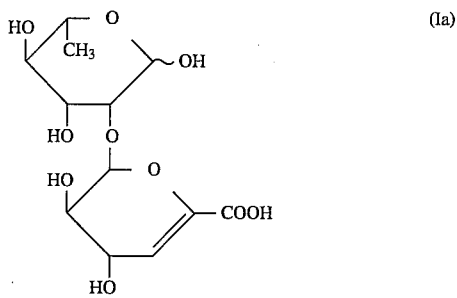

or a salt thereof.

12. A process as defined in claim 11, wherein the plant seeds are those of a plant selected from the group consisting of slender amaranth, asparagus, oat, barnyard grass, rice, green foxtail, pea, timothy grass, Persian speedwell(bird's-eye speedwell), okra, wild oat, goose grass, turnip, pumpkin, cauliflower, cabagge, cress, cockscomb, cockspur grass, rice flat-sedge, burdock, "shikokubie", perifla, crown daisy, common putslane, celery, buckwheat, radish, "ta-inubie", small-flower umbrella-plant, cayenne pepper, corn, tomato, eggplant, leek, carrot, Chinese cabbage, parsley, sunflower, amaranth, broccoli, spinach, hardstem bulrush, matricaria, trefoil, cabgrass and lettuce.

13. A method for culture, wherein an artificial soil or a culture solution contains compound(s) represented by the following formula (Ic):

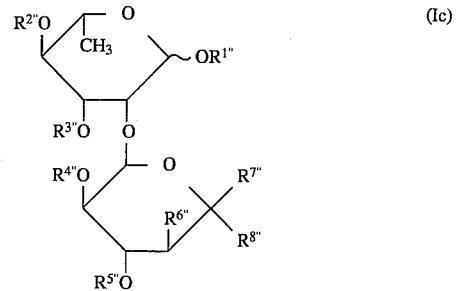

wherein $R^{1''}$, $R^{2''}$, $R^{3''}$, $R^{4''}$, and $R^{5''}$ independently represent a hydrogen atom or an acetyl group, $R^{6'}$ represents a hydrogen atom or a hydroxyl group, $R^{7''}$ represents a hydrogen atom, or $R^{6''}$ and $R^{7''}$ together may represent another direct bond, and $R^{8''}$ represents a carboxyl, methoxycarbonyl, or hydroxymethyl group, or salt(s) thereof.

14. A method for culture, wherein an artificial soil or a culture solution contains the compound represented by the following formula (Ia):

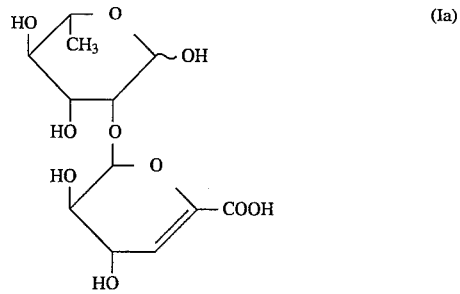

or a salt thereof.

15. A method as defined in claim 14, wherein the content of the compound represented by formula (Ia) or salt(s) thereof is from 1 to 10000 ppm.

16. A method for the growth inhibition of moyashi roots, which comprises applying a solution containing compound(s) represented by formula (Ic) or salt(s) thereof to moyashi seeds.

17. A method for the growth inhibition of moyashi roots, which comprises applying a solution containing the compound represented by formula (Ia) or salt(s) thereof to moyashi seeds.

18. A method for the growth promotion of moyashi hypocotyls, which comprises applying a solution containing compound(s) represented by formula (Ic) or salt(s) thereof to moyashi seeds.

19. A method for the growth promotion of moyashi hypocotyls, which comprises applying a solution containing the compound represented by formula (Ia) or salt(s) thereof to moyashi seeds.

According to the present invention, there are provided physiologically active substances with a new structure useful for the growth regulation of agricultural products etc., a novel culture method effective for the growth of plants, and a method for the industrial production of moyashi of enhanced value as a commercial product in high productivity.

DESCRIPTION OF THE FIGURES

FIG. 1 also shows the results of gibberellin ($GA_3$) and indoleacetic acid (IAA).

FIG. 4 shows lettuces cultured in water only (control) and water containing the present compound in an amount derived from 50, 100, 150, and 200 sunflower seeds (from left to right).

FIG. 5 shows peas cultured in water only (control) and water containing the present compound in an amount derived from 50, 100 and 150 sunflower seeds (from left to right).

FIG. 6 shows tomatoes cultured in water only (control) and water containing the present compound in an amount derived from 50, 100 and 150 sunflower seeds (from left to right).

FIG. 7 shows black matpes cultured in water only (control) and water containing the present compound in an amount derived from 150, 500, and 1500 sunflower seeds (from left to right).

FIG. 8 shows untreated green gram (control) at the right and green gram treated with the present compound at the left.

DETAILED DESCRIPTION OF THE INVENTION

Figure 1B:
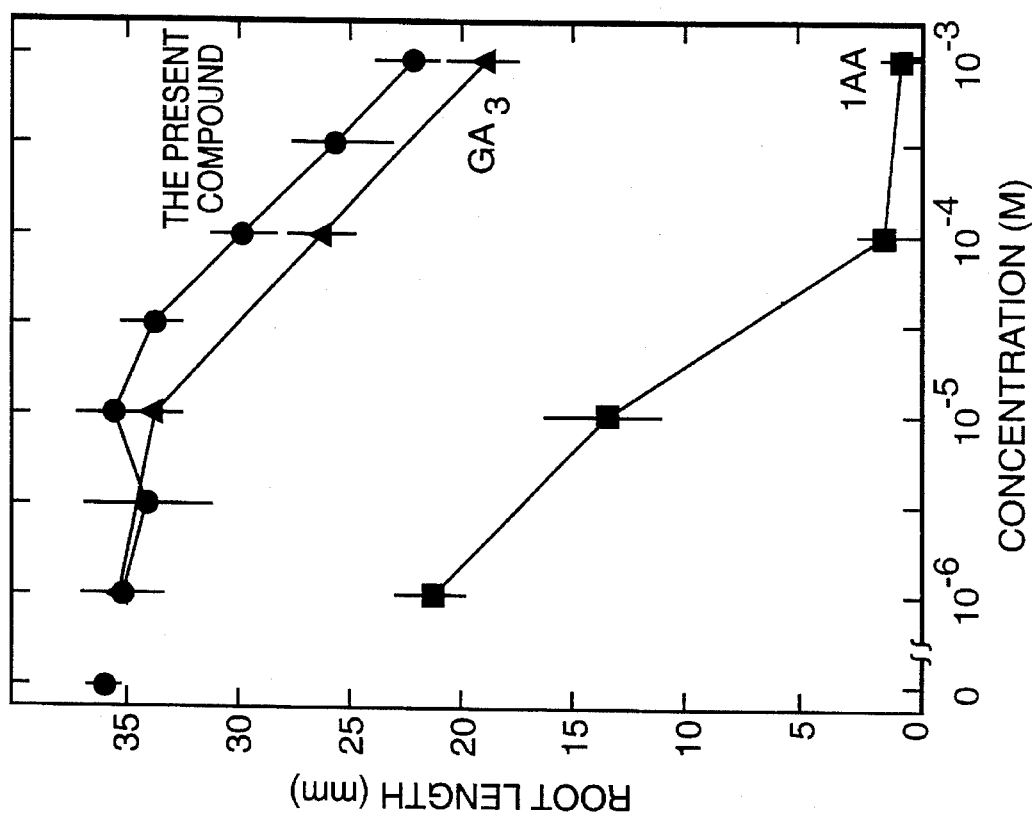
FIG. 1 shows the effect of a sodium salt of compound (Ia) on the growth of hypocotyls (part of a plant above the ground) and roots.

Salts of compounds represented by the above formula (I), (Ia), (Ib), or (Ic) include e.g. sodium salts and potassium salts, lithium salts.

Compounds represented by the above formula (I), (Ia), (Ib), or (Ic) or salts thereof can be obtained by the following chemical synthesis.

As illustrated in the reaction scheme below, α-L-rhamnose is first allowed to react with benzyl alcohol in the presence of a catalytic amount of sulfuric acid in a solvent such as benzene etc., thus giving benzyl glycoside, which in turn is allowed to react with 2,2-dimethoxypropane in a solvent such as acetone etc. in the presence of p-toluenesulfonic acid, thereby being converted into isopropylidene (compound (2)). Compound (2) is then allowed to react with benzyl bromide in the presence of sodium hydride in a solvent e.g. N,N-dimethylformamide etc., thereby giving compound (3), followed by treatment with acetic acid-water-1,4-dioxane etc. for the elimination of the isopropylidene residue, so that Compound (4) is obtained.

Subsequently, compound (4) is treated with dibutyltin oxide (Bu$_2$SnO) in a solvent such as benzene etc., thereby forming compound (5), which is then treated with benzyl bromide in the presence of cesium fluoride (CsF), whereby compound (6) is obtained:

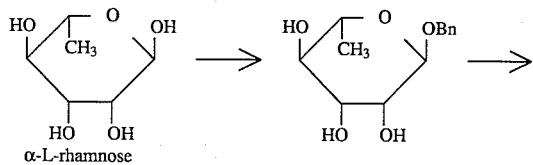
α-L-rhamnose

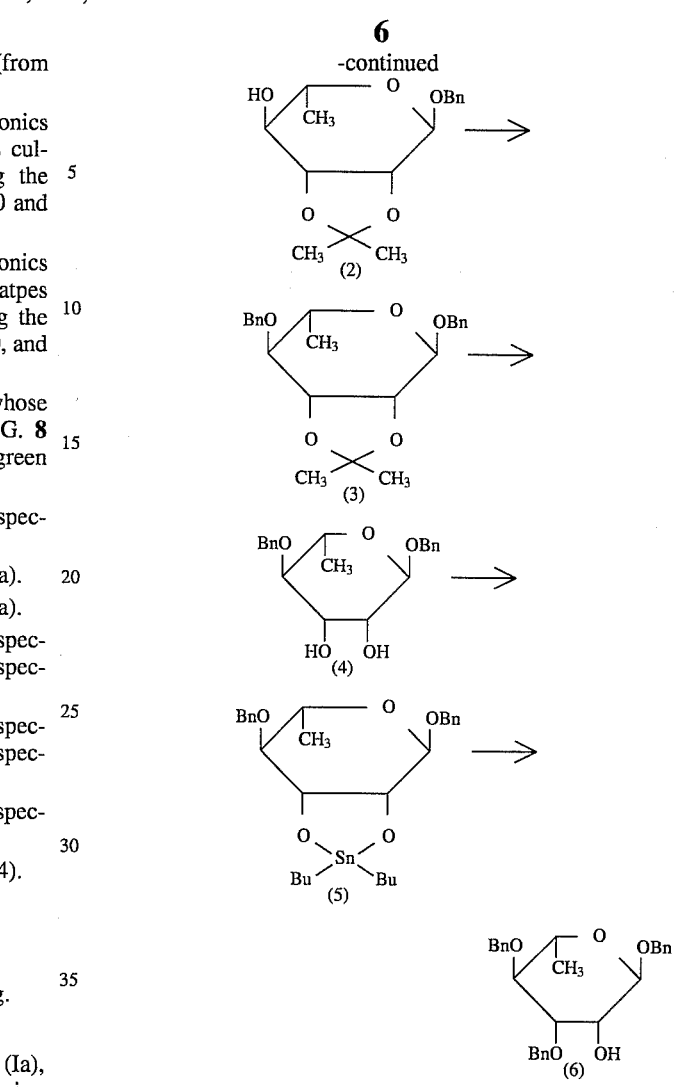

wherein Bn represents a benzyl group, and Bu represents a n-butyl group.

As illustrated in the following reaction scheme, compound (6) is then allowed to react compound (A) in the presence of molecular sieve and methylsulphenyl bromide, whereby compound (7) can be obtained. The compound used in this step, compound (A), is a known compound which can be synthesized in a 7-step reaction from D-glucose (Acta Chem. Scand., 43, 471 (1989); Carbohydr. Res., 202, 225 (1990)).

Compound (7) is then treated with a base e.g. potassium carbonate etc. in a solvent such as methanol etc., whereby compound (8) can be obtained. Compound (8) is catalytically reduced with palladium, palladium-carbon, palladium hydroxide, etc., thereby being converted into compound (8a).

Subsequently, compound (8) is treated with (1) sulfur trioxide (SO$_3$)-pyridine in dimethylsulfoxide (DMSO) and trimethylamine and then (2) sodium chlorite and sodium dihydrogen phosphate in t-butyl alcohol-water-2-methyl-2-butene, so that compound (9) can be obtained. Compound (9) is catalytically reduced with palladium, palladium-carbon, palladium hydroxide, etc., thereby being converted into compound (9a).

Subsequently, compound (9) is treated with trimethylsilyidiazomethane in a solvent such as benzene-methanol etc., whereby compound (10) can be obtained. Compound (10) is catalytically reduced with palladium, palladium-carbon, palladium hydroxide, etc., to be converted into compound (10a).

Subsequently, compound (10a) is acetylated with acetic anhydride-pyridine etc., thereby giving compound (11), followed by treatment with 1,8-diazabicyclo[5.4.0.]-7-undecene (DBU) in a solvent e.g. pyridine, whereby compounds (12) and (12') are formed. Compounds (12) and (12') are then hydrolyzed with a base such as sodium hydroxide, sodium methoxide, sodium ethoxide, sodium t-butoxide, etc., whereby compound (1) can be obtained.

Alternatively, compounds (12) and (12') are catalytically reduced with palladium, palladium-carbon, palladium hydroxide, etc., to be converted into compound (13), which in turn is hydrolyzed with a base, such as sodium hydroxide, sodium methoxide, sodium t-butoxide, etc., whereby compound (14) can be obtained.

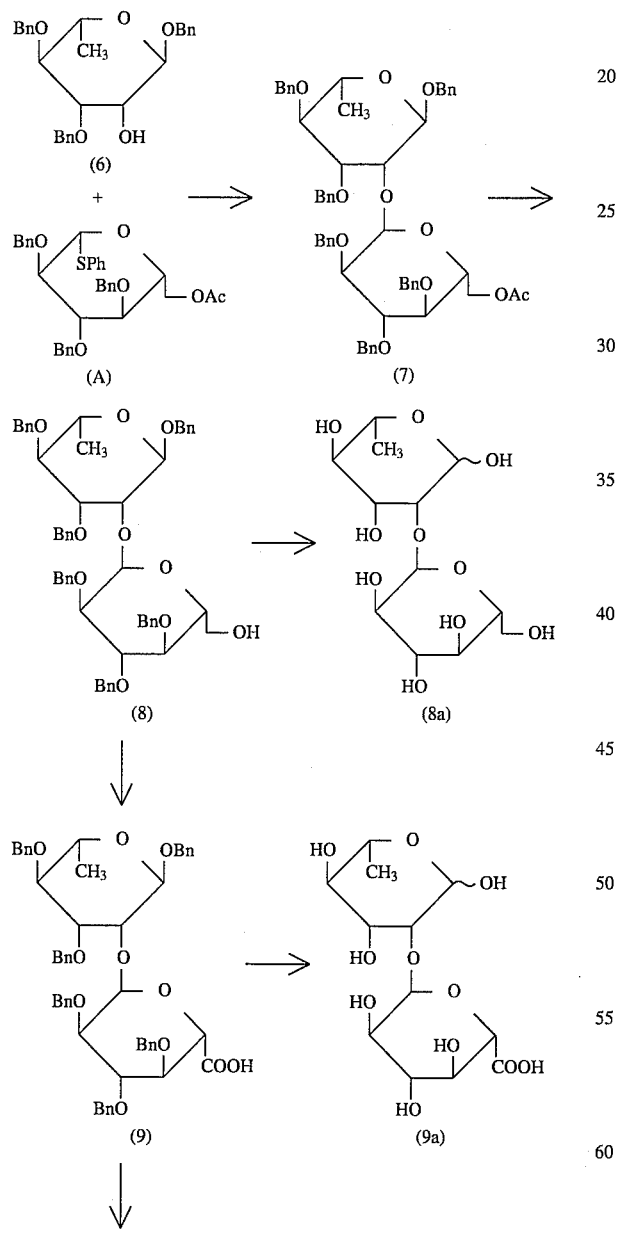

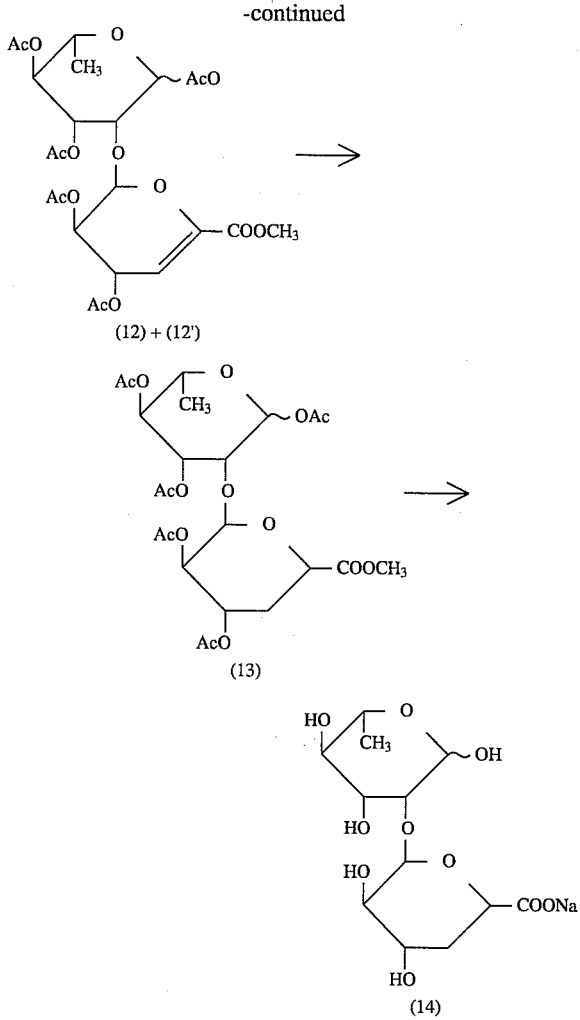

wherein Ac represents an acetyl group, Ph represents a phenyl group, and Bn possesses the same meaning as defined above.

Carboxylic acids thus obtained, such as compounds (9), (9a), etc. can be converted into the corresponding salts according to a conventional method; and sodium salts, such as compounds (1), (14), etc., can be converted into the corresponding free carboxylic acids or other salts according to a conventional method.

Out of the present compounds represented by the above formula (I), the compound wherein $R^1$, $R^2$, $R^3$, $R^4$, and $R^5$ each represent a hydrogen atom, and $R^6$ and $R^7$ represents another direct bond, and $R^8$ represents a carboxyl group, i.e. the compound of the above formula (Ia) or its salt, can also be obtained by isolation and purification from cress seedlings.

In the isolation and purification of compound (Ia), cress seeds obtained e.g. from a commercial source or a natural source or by culture thereof may be used as starting material.

Compound (Ia) can be isolated and purified from the culture solution of cress seeds germinated in hydroponics.

Culture form in hydroponics is particularly not limited as far as cress plant seeds can be germinated.

Usually, cress plant seeds are germinated in the dark under aeration. Culture temperature is usually 15° to 30° C., preferably 20° to 25° C. Culture time is usually 1 to 2 days. The composition of a culture for hydroponics is particularly not limited, but water free from any additive is preferably employed for the efficient isolation and purification of compound (Ia). Before culture, cress plant seeds are preferably immersed in water, so that the amount of compound (Ia) secreted can be increased.

The culture solution thus obtained is concentrated in a usual manner and is then applied as necessary to gel filtration chromatography, high-performance liquid chromatography, etc., or a combination thereof, whereby compound (Ia) can be purified.

Besides the above cress plant, compound (Ia) can also be obtained by immersing in water seeds of a plant selected from the group consisting of slender amaranth, asparagus, oat, barnyard grass, rice, green foxdtail, pea, timothy grass, Persian speedwell, okra, wild oat, goose grass, turnip, pumpkin, cauliflower, cabagge, cress, cockscomb, cockspur grass, rice flat-sedge, burdock, "shikokubie", perilla, crown daisy, common purslane, celery, buckwheat, radish, "ta-inubie", small-flower umbrella-plant, cayenne pepper, corn, tomato, eggplant, leek, carrot, Chinese cabbage, parsley, sunflower, amaranth, broccoli, spinach, hardstem bulrush, matricaria, trefoil, cabgrass, and lettuce, followed by collecting from the extract the compound (Ia) or a salt thereof. The source of these seeds is not particularly limited, and it is possible to employ seeds obtained e.g. from a commercial source or a natural source or by culture thereof.

Usually, cress plant seeds are germinated in the dark under aeration. Regardless of whether the seeds are to be germinated or not, temperature for immersion is usually 15° to 30° C. preferably 20° to 25° C. Immersion time is usually 1 to 2 days.

Tap water as well as distilled water may be used as water for immersion, but distilled water is preferably employed so as not to affect the physiological activity of compound (Ia).

The immersion solution thus obtained is concentrated in a usual manner and then applied as necessary to gel filtration chromatography, high-performance liquid chromatography. etc., or a combination thereof, whereby compound (Ia) can be purified.

Out of the present compounds thus obtained compounds (Ic) or salts thereof are physiologically active substances with "allelopathy" which promote the growth of hypocotyls of a wide variety of plants and which promote the growth of their roots at a low concentration whereas inhibit the growth of their roots at a high concentration. These compounds are useful as components in a treatment solution such as spray solution, immersion solution, etc., for use in a wide variety of culture methods, particularly for culture using an artificial soil (e.g. vermiculite), hydroponics, and a method for the growth inhibition of moyashi roots, as well as a method for the growth promotion of moyashi hypocotyls.

For use of compound (Ic) or a salt thereof as a component in an artificial soil or culture solution, the content is usually 1 to 10,000 ppm, preferably 100 ppm or more. Other effective components in the artificial soil or culture solution can be suitably selected depending on the type of plant to be cultured. It is also possible to adopt components conventionally used in an artificial soil, a culture solution, etc.

The plants to which the present cultivation method can be applied are not particularly limited as far as they can be cultured in an artificial soil or culture solution. Specific examples to which the present method is applicable are tomato, lettuce, and cabbage. However, the present method is not limited to such plants, as stated above.

A desired plant can be cultured in an artificial soil or culture solution containing compound (Ic) or a salt thereof. Culture conditions other than those of said artificial soil or culture solution can be suitably determined depending on the type of plant to be cultured.

In case compound (Ia) (or a salt thereof) derived from the above plants is used, it can be used in the form of an extract (immersion solution) as such without isolation/purification.

In case compound (Ia) or a salt thereof is used for the growth inhibition of moyashi roots or the growth promotion of moyashi hypocotyls, a solution containing 1 to 10000 ppm compound (Ic) or salt thereof is preferably sprayed or spread downwards on germinated moyashi, or otherwise germinated moyashi on the second day of culture is preferably immersed only once in a solution containing 1 to 10000 ppm compound (Ic) or salt thereof. This method differs from conventional hydroponics and is characterized by spraying or sprinkling a solution containing compound (Ic) or a salt thereof, or by only once immersion in said solution for a short period of time.

For the present method for the growth inhibition of moyashi roots and for the growth promotion of moyashi hypocotyls, compounds (Ia) or salts thereof derived from said plants can be used in the form of an plant extract solution (immersion solution) as such without isolation/purification.

EXAMPLES

The present invention is further illustrated with reference to the following examples, but these examples are not intended to limit the scope of the present invention.

(Example 1)

Isolation and purification of the present compound from cress seeds (1) Preparation of plant materials 3000 cress (*Lepidium sativum L.*) seeds were immersed for 1 hour in deionized water.

Then, the cress seeds were placed on a stainless mesh, and this stainless mesh was gently placed in a stainless dish (40×40×3 cm$^3$) containing 1.6 l deionized water. The cress seeds were cultured at 25° C. for 2 days in the dark under aeration with an air pump.

(2) Purification of the present compound

① First, the cress plant culture solution obtained in (1) above was filtered through Toyo No. 1 filter paper, and the filtrate was concentrated at 35° C. under reduced pressure. Then, the concentrate was partitioned into acetone soluble and insoluble phases.

*Amaranthus caudatus* L. seeds were gently placed on a filter paper immersed with 0.8 ml of a sample solution (from said soluble or insoluble fraction) in a Petri dish of 3 cm diameter and were then allowed to stand at 25° C. for 5 days in the dark, and the lengths of germinated hypocotyls and roots were determined for the evaluation of whether or not any biological activity on plant growth was present in the acetone soluble and/or insoluble phases.

As a result, the activity showing the growth promotion of hypocotyls and the growth inhibition of roots (of *Amaranthus caudatus* L.) was confirmed to be present in the acetone insoluble fraction.

Subsequently, the acetone insoluble fraction was dissolved in 10 ml water and then separated by molecular exclusion chromatography (Mol cut, Millipore Corp.) into three fractions, i.e. $M_r$ above 100,000, 5,000–100,000, and below 5,000. The biological activity was found to be present in the fraction of $M_r$ below 5,000. This fraction was concentrated at 35° C. under reduced pressure.

② The concentrate (approx. 150 mg) obtained in ① above was dissolved in water and then purified by high performance liquid chromatography (HPLC) (Waters. μ Bondasphere 5 μ C$_{18}$–100 Å; column 19 mm×15 cm; eluent 100 % H$_2$O, flow rate 5 ml/min; 214 nm detector). The above biological activity was found in fractions of retention time of 5–8 minutes.

Said HPLC fractions were combined and concentrated at 35° C. under reduced pressure and further purified by HPLC (SIC Packed Column AQ-324 S-5 120A ODS; YMC Co. Ltd.; eluent 100 % H$_2$O, flow rate 1 ml/min; 214 nm detector). The above biological activity was found in fractions of retention time of 17.0–17.8 minutes. These fractions were combined and concentrated at 35° C. under reduced pressure, whereby 6.5 mg amorphous powder was obtained.

③ Structural determination of the present compound

The purified sample thus obtained was analyzed for structural determination. Optical rotation was determined with a JASCO A-202 spectrophotometer. IR spectrum was obtained in glycerol with a JASCO A-202 spectrophotometer. UV spectrum was obtained in D$_2$O with a JASCO UVIDEC-610A spectrophotometer. $^1$H-NMR spectrum was obtained with JEOL JNM-GX400 NMR spectrometer. FAB mass spectrum was recorded in glycerol matrix.

① Optical rotation: $[\alpha]_D^{19}$=+87.8 (c 0.032, D$_2$O)

② IR: Peaks were found at the absorption of —COOH group (1590 cm$^{-1}$) and OH group (3300 cm$^{-1}$).

③ $\lambda_{max}$ 225 nm (εapprox. 2,100)

④ Mass: A M$^+$+Na peak was observed at m/z 367.0591.

⑤ $^1$H-NMR: δ5.72 (1H, d, J=3.2 Hz, j), 5.17 (1H, d, J=1.6 Hz, a), 5.07 (1H, d, J=2.3 Hz, g), 4.26 (1H, dd, J=6.9, 3.2 Hz, i). 4.08 (1H, dd, J=3.4, 1.6 Hz, b), 3.79 (1H, dq, J=9.7, 6.8 Hz, e), 3.76 (1H, dd, J=9.7, 3.4 Hz, c), 3.72 (1H, dd, J=6.9, 2.3 Hz, h) 3.31 (1H, dd. J=9.7 Hz, d) and 1.80 (3H, d, J=6.8 Hz, f)

⑥ After treated overnight with acetic anydride-pyridine-MeOH at room temperature, the above purified sample was converted into the corresponding methyl ester having five acetoxy groups. The result of mass spectrum analysis indicated that the molecular formula of this ester is C$_{23}$H$_{30}$O$_{15}$ [m/z 546.1564 (M$^+$)].

The IR spectrum indicated no hydroxyl absorption. The $^1$H-NMR(CDCl$_3$) spectrum exhibited signals for five acetoxyl methyl protons [δ2.00 (3H, s), 2.05 (3H, s), 2.10 (3H, s), 2.14 (3H×2, [s] and signal for methoxyl proton [δ3.88 (3H, s)].

The following results were obtained in nuclear Overhauser effect (NOE) experiments of the methyl ester. That is, irradiation at δ5.17 (H at the 1-position) increased 7.3 % and 8.3% the intensity of H at the 2-position and H at the 1-position, respectively.

Irradiation at δ5.07 (H at the 1'-position) increased 8.3%, 6.9%, and 13.6% the intensity of H at the 1-, 2-, and 2'-positions, respectively.

⑥ These results indicated that this purified sample is sodium 2-0-rahmnopyranosyl- 4-deoxy-threo-hex-4-enopyranosiduronate represented by the above formula (Ia), i.e. the sample proved to have the structure of the above formula (I).

④ Determination of biological activity of the present compound

Figure 1A:
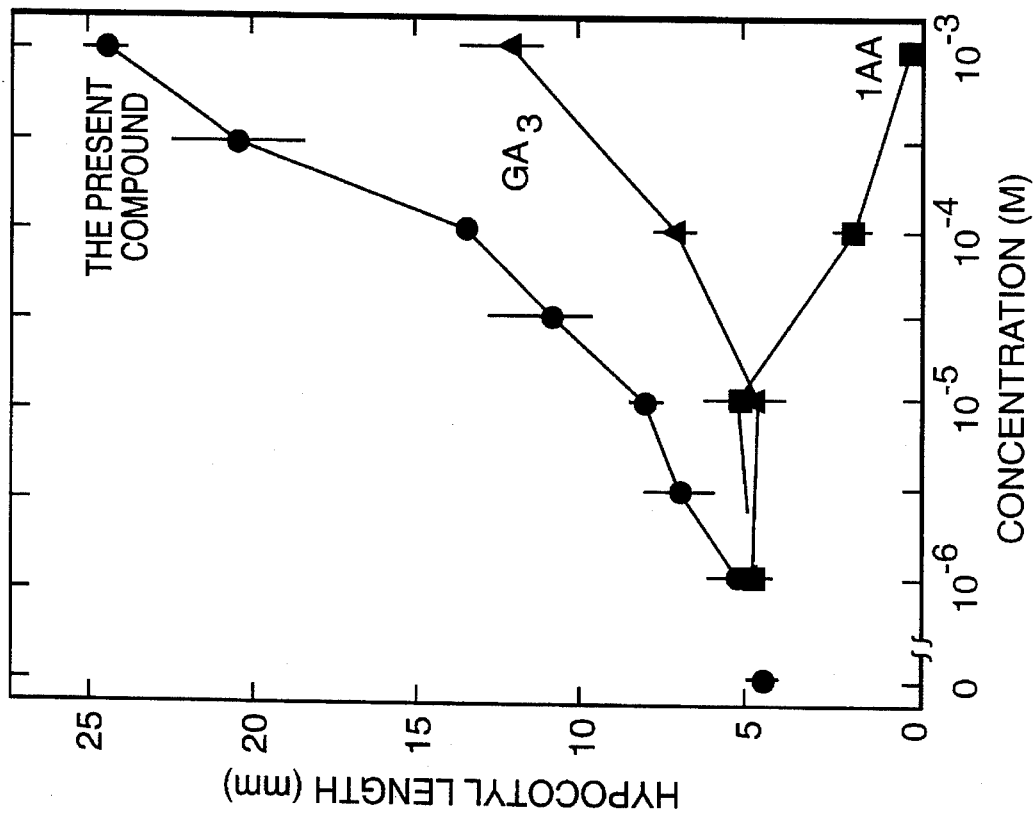

The effect of the present compound (1) on the growth of etiolated *Amaranthus caudatus* L. seedlings was examined in comparison with that of gibberellin (GA$_3$) and indoleacetic acid (IAA). Determination was carried out according to the method as described in (2) ① above. The results are shown in FIG. 1. From the results, it was found that the present compound promotes the hypocotyl growth at concentrations higher than 3 μM and inhibits the root growth at concentrations higher than 100 μM. The growth promotion of hypocotyls by the present compound is twenty to thirty times as much as that by gibberellin, suggesting that the present compound is a potent growth substance. The growth inhibition of roots by the present compound was almost the same as that of gibberellin. Indoleacetic acid inhibited the hypocotyl and root growth.

(Example 2)

Isolation and purification of the present compounds from plant seeds other than cress
(1) Preparation of plant materials 900 seeds each of 19 kinds of plants, i.e. sunflower, spinach, corn, okra, carrot, oat, parsley, barnyard grass, cayenne pepper, buckwheat, tomato, cabbage, lettuce, cockscomb, burdock, trefoil, pea, radish, and Persian speedwell seeds were immersed for 1 hour in deionized water. Subsequently, these seeds were placed on a stainless mesh, and this stainless mesh was gently placed in a stainless dish (40×40×3 cm$^3$) containing 1.6l deionized water. These seeds were then cultured at 25° C. for 2 days in the dark under aeration with an air pump.
(2) Purification of the present compounds ① Each seed immersion solution obtained in (1) above was filtered through Toyo No. 1 filter paper, and each filtrate was concentrated at 35° C. under reduced pressure. Then, said concentrate was partitioned into acetone soluble and insoluble phases. *Amarantus caudatus* L. seeds were gently placed on a filter paper immersed with 0.8 ml of a sample solution (from an acetone soluble or insoluble fraction) in a Petri dish of 3 cm diameter and were then allowed to stand at 25° C. for 5 days in the dark. and the lengths of germinated hypocotyts and roots were determined for the evaluation of whether or not any biological activity on plant growth is present in the acetone soluble and insoluble phases.

As a result, the activity showing the growth promotion of hypocotyls and the growth inhibition of roots (of *Amaranthus caudatus* L.) was confirmed to be present in the acetone insoluble fraction.

Subsequently, the acetone insoluble fraction was dissolved in 10 ml water and then separated by molecular exclusion chromatography (Mol cut, Millipore Corp.) into three fractions, i.e. $M_r$ above 100,000, 5,000–100,000, and below 5,000. The biological activity was found to be present in the fraction of $M_r$ below 5,000. This fraction was concentrated at 35° C. under reduced pressure.

② Each concentrate (about 150 mg) obtained in ① above was dissolved in water and purified by HPLC (Waters, μ Bondasphere 5 μ $C_{18}$–100 Å; column 19 mm×15 cm; eluent 100% $H_2O$, flow rate 5 ml/min; 214 nm detector). The above biological activity was found in fractions of retention time of 5–8 minutes. The retention time agreed with the retention time (in HPLC under the same conditions) of the compound obtained in Example 1 from the cress seedlings.

Said HPLC fractions were combined and concentrated at 35° C. under reduced pressure and further purified by HPLC (YMC Packed Column AQ-324 S-5 120A ODS; YMC Co. Ltd.; eluent 100% $H_2O$, flow rate 1 ml/min; 214 nm detector). The above biological activity was found in fractions of retention time of 17.0–17.8 minutes. These fractions were combined and concentrated at 35° C. under reduced pressure, whereby a small amount of amorphous powder (several mg) originating in each plant was obtained.
(3) Determination of biological activities of the present compounds ① Out of the above purified compounds, the compound derived from sunflower seeds was mixed with 47 g vermiculite, and this vermiculite was placed in a vessel of 9 cm diameter, and *Amaranthus caudatus* L., lettuce, Persian speedwell, and timothy seeds were scattered in this vessel and grown at 25° C. over 3 weeks in the sunlight for 16 hours per day.

Figure 2:
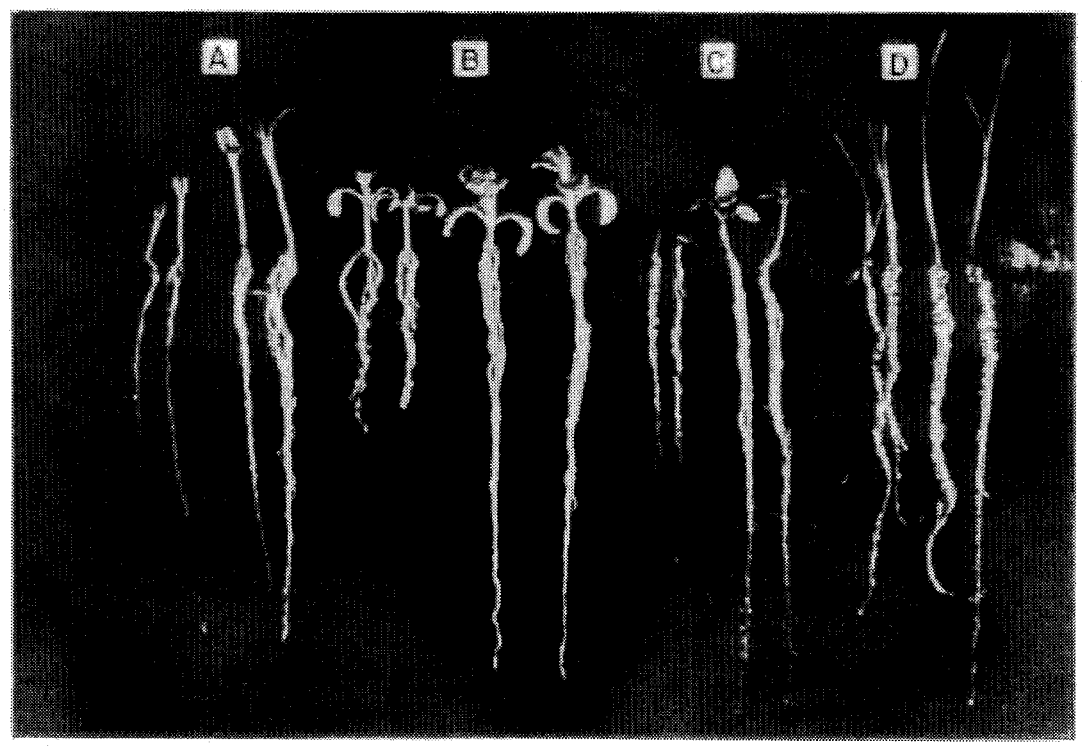
FIG. 2 is a photograph of plants whose growth was promoted by the present compound obtained by extraction of sunflower seeds.

The result indicated that the hypocotyl growth of every plant was promoted about 2 times as high as the corresponding control at each left in (A) to (D), as can be seen from the photograph of seedlings in FIG. 2. In addition, it was made evident that at a low concentration of 100 ppm, the growth of roots excluding those of the simple leaf plant timothy was also promoted about 2 times as high as the control.

② Each of the above compounds (in an amount of the compound derived from 10 seeds) originating in cress seeds and 19 kinds of plants (sunflower etc.) seeds was dissolved in 1 ml distilled water, and the sample solution was then put in a vessel of 3.3 cm diameter without a filter paper, and *Amaranthus caudatus* L. seeds were scattered thereon and grown at 25° C. for 5 days in the dark.

Figure 3:
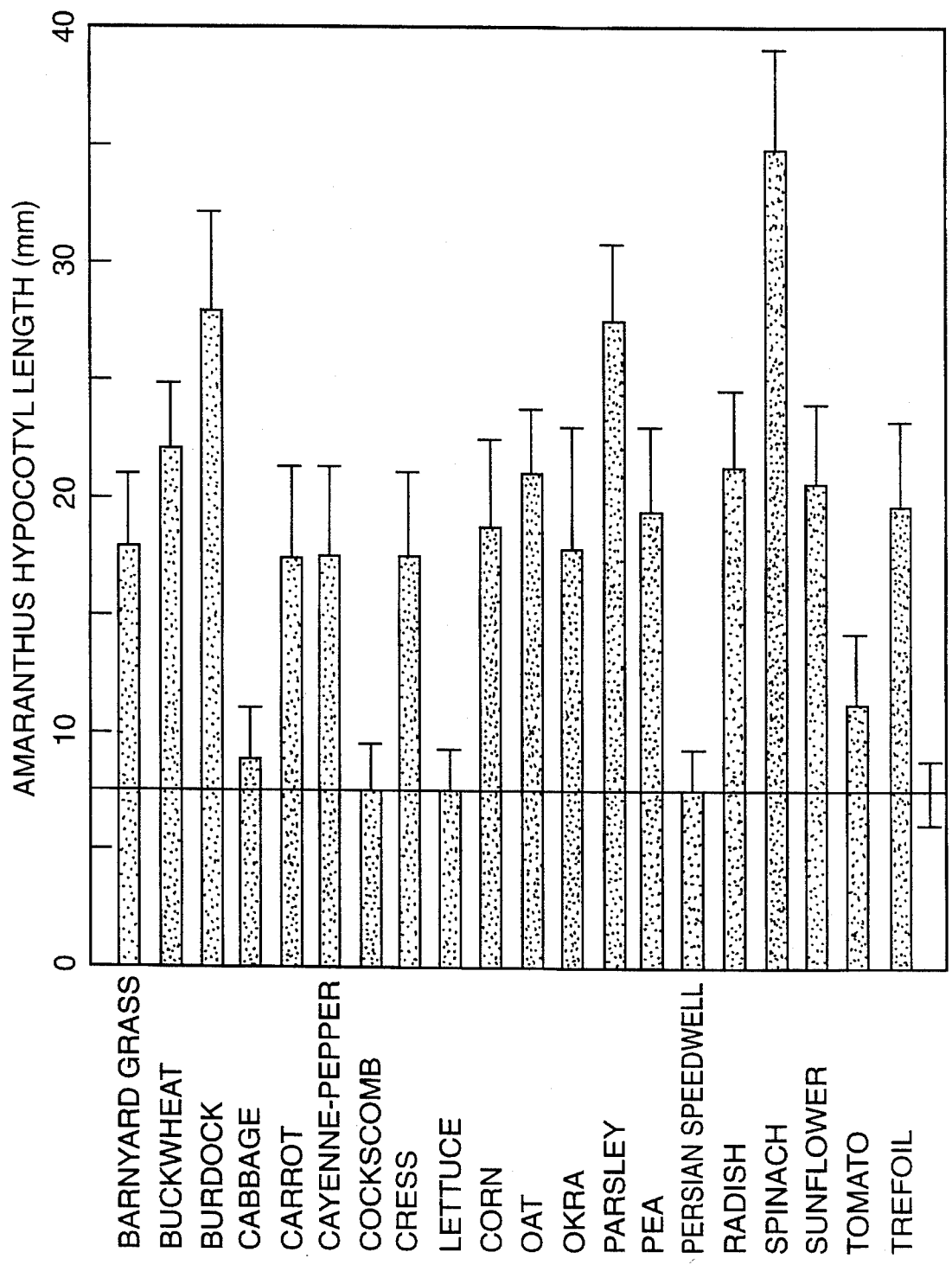
FIG. 3 shows the results of plant growth promotion on 20 kinds of plant seeds by the present compound obtained by extraction of sunflower seeds.

As a result, the hypocotyl growth of a number of plants, similar to ① above, was promoted even in this experimental system, as shown in FIG. 3. The growth promotion activity was relatively low in the cases of lettuce, *Amaranthus caudatus* L., tomato, and Persian speedwell, but the same growth promotion-activity was exhibited by increasing 10 times as high concentration as the original, so that the growth promotion activity is considered to be a common phenomenon among said 19 kinds of plants.

(Example 3)

Promotion activity of the hypocotyl elongation of *Amaranthus caudatus* L. seedlings in a secretion solution from germinated seeds 10 seeds each of 44 kinds of plants, slender amaranth etc., were sterilized for 30 minutes in 1% aqueous sodium hypochlorite solution, followed by washing with tap water for 30 minutes and then with distilled water. The moist seeds were placed in a vessel (3.3 cm diameter) containing 1 ml water and were then cultured at 25° C. in the dark. In the case of large seeds such as corn, pea, and oat seeds, a vessel of 6 cm diameter was employed and 3 ml distilled water was added. After 2 days of culture, the secretion solution was transferred to a vessel with a filter paper (Toyo filter paper No. 1), and 10 seeds of *Amaranthus caudatus* L. were scattered. After cultured at 25° C. for 5 days in the dark, the length of *Amaranthus caudatus* L. hypocotyls germinated was determined. In case plant seeds indicated little or no hypocotyl growth promotion in the above test, a few secretion solutions were prepared from a greater number of seeds. e.g. 50, 100, or 150 seeds, and were used in an *Amaranthus caudatus* L. hypocotyl elongation test. As the control, distilled water was used in place of the secretion solution.

The results are shown in Table 1.

TABLE 1

| Plants | *Amaranthus caudatus* L. | hypocotyl elongation (mm ± S.E.) | |
|---|---|---|---|
| | 10 seeds | 50 seeds | 100 seeds |
| slender amaranth | 7.8 ± 1.5 | 8.3 ± 1.0 | 10.9 ± 0.8 |
| asparagus | 11.1 ± 1.4 | | 15.3 ± 2.0 |
| barnyard grass | 15.9 ± 3.1 | | |
| rice | 15.0 ± 2.9 | | |
| green foxtail | 15.0 ± 1.9 | | |
| pea | 19.5 ± 2.8 | | |
| timothy grass | 7.9 ± 1.6 | | 11.8 ± 1.4 |

TABLE 1-continued

| Plants | *Amaranthus caudatus* L. 10 seeds | hypocotyl elongation (mm ± S.E.) 50 seeds | 100 seeds |
|---|---|---|---|
| Persian speedwell | 11.5 ± 2.0 | 13.3 ± 1.7 | |
| okra | 21.8 ± 5.4 | | |
| wild oat | 20.7 ± 3.0 | | |
| goose grass | 7.9 ± 1.7 | 11.6 ± 1.1 | |
| turnip | 8.2 ± 1.6 | | 12.9 ± 2.7 |
| pumpkin | 17.2 ± 4.0 | | |
| cauliflower | 9.2 ± 2.4 | | 12.2 ± 1.2 |
| cabagge | 5.6 ± 1.0 | 10.8 ± 1.6 | |
| cress | 19.4 ± 1.5 | | |
| cockspur grass | 7.7 ± 1.9 | 12.5 ± 1.5 | |
| rice flat-sedge | 8.7 ± 1.5 | 10.7 ± 1.4 | |
| burdock | 28.5 ± 4.8 | | |
| "shikokubie" | 15.6 ± 2.4 | | |
| perilla | 12.4 ± 2.5 | | 18.0 ± 2.2 |
| crown daisy | 17.8 ± 3.6 | | |
| common purslane | 9.7 ± 2.0 | 10.5 ± 1.3 | |
| celery | 8.9 ± 2.0 | | 20.0 ± 3.2 |
| buckwheat | 21.7 ± 3.2 | | |
| radish | 21.6 ± 2.8 | | |
| "ta-inubie" | 17.2 ± 2.1 | | |
| small-flower umbrella-plant | 9.2 ± 2.3 | 10.2 ± 1.0 | |
| corn | 19.0 ± 2.5 | | |
| tomato | 11.0 ± 2.9 | 16.9 ± 3.0 | |
| eggplant | 16.2 ± 2.8 | | |
| leek | 19.8 ± 4.3 | | |
| carrot | 17.7 ± 3.6 | | |
| chinese cabbage | 8.1 ± 2.7 | | 12.4 ± 2.0 |
| parsley | 27.3 ± 4.9 | | |
| sunflower | 20.9 ± 4.9 | | |
| amaranth | 7.8 ± 1.6 | 12.8 ± 1.9 | |
| broccoli | 13.4 ± 2.7 | | |
| spinach | 34.8 ± 5.4 | | |
| hardstem bulrush | 9.0 ± 2.1 | 9.6 ± 1.0 | *14.5 ± 2.8 |
| matricaria | 6.8 ± 1.7 | 10.7 ± 1.5 | |
| trefoil | 19.7 ± 4.3 | | |
| cabgrass | 12.7 ± 2.1 | | |
| lettuce | 7.8 ± 1.5 | 10.0 ± 1.0 | |
| Control | 8.3 ± 1.5 | 7.8 ± 1.0 | 7.6 ± 1.2 |

*150 seeds were used.

The secretion solutions from spinach, burdock, and parsley exhibited a particularly strong promotion activity of hypocotyl elongation. The secretion solutions from 13 kinds of plants, i.e. buckwheat, radish, sunflower, oat, leek, trefoil, pea, cress, corn, okra, crown daisy, carrot, "ta-inubie" exhibited a relatively strong activity. The secretions solution from 20 kinds of plants, i.e. slender amaranth, asparagus, timothy grass, etc., exhibited a weak activity.

From the above results, 44 kinds of plants set forth in Table 1 proved to secret the present compound (1) having a hypocotyl elongation promotion activity, and it is understood that the present compound (1) can be obtained by extraction of their seeds or from their secretion solution.

(Example 4)

Hydroponics in the presence of the present compound
A. Preparation of a sunflower secretion solution A secretion solution was prepared from 2000 sunflower seeds using 2 l water in the same manner as in Example 2. The secretion solution was concentrated under reduced pressure, whereby four concentrated extracted solution of a predetermined concentration expressed in terms of the number of sunflower seeds (50 to 200 seeds) were prepared, and the final volume of each aqueous solution was adjusted to 20 ml for use in a hydroponics experiment.

B. Method for hydroponics

Tomato, lettuce, pea, and cabbage were selected as test plants, and their seeds were seeded and then incubated at 25° C. for 2 days (3 days for tomato) in the cycle of 12 hours in the dark and 12 hours in the bright. Then, the seedlings were transplanted to a hydroponics chamber made of glass (28 mm diameter, 40 mm height, and 20 ml volume) and subjected to hydroponics for 7 days at 25° C. in the cycle of 12 hours in the bright and 12 hours in the dark. The seedlings were then examined for lower and upper. hypocotyl length, root length, leaf size, and weight.

(1) Lettuce hydroponics

According to the same method as described above, a hydroponics experiment was made using four secretion solutions containing the present compound (1) (referred to as "lepidimoide", hereinafter) at a predetermined concentration expressed in terms of the number of sunflower seeds (i.e., 50, 100, 150, and 200 seeds) and a lepidimoide-free control. 7 days thereafter, the weight and length of hypocotyls and roots were determined for the evaluation of the effect on plant growth.

Figure 4:
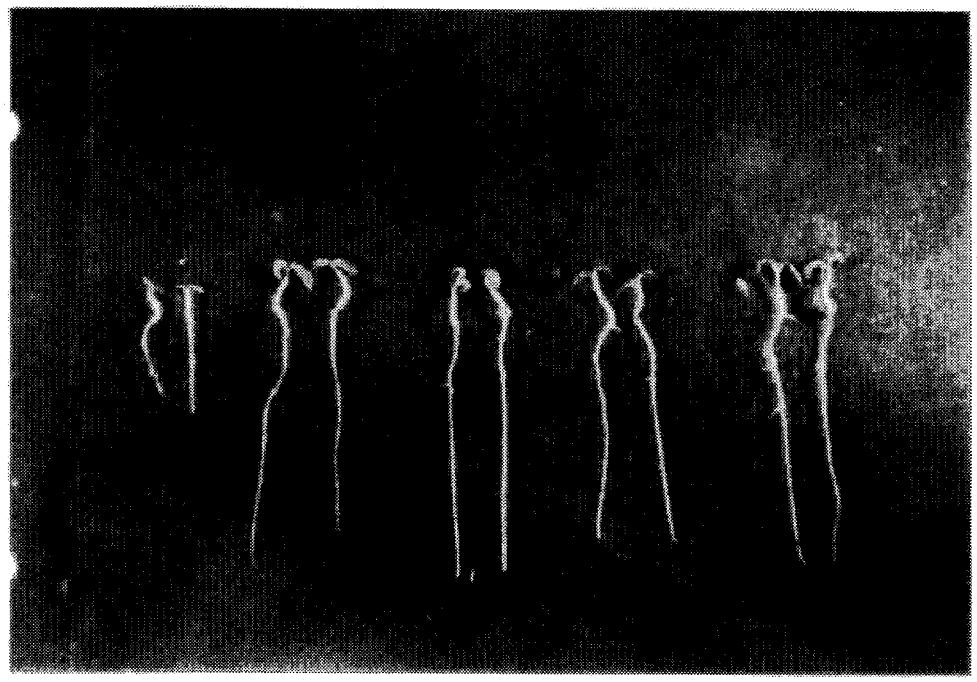
FIG. 4 is a photograph of lettuces after hydroponics using the present compound.

The results are set forth in Tables 2 and 3 and FIG. 4.

TABLE 2

Measurement results of hypocotyl and root lengths

| | Hypocotyl length | | Root length | |
|---|---|---|---|---|
| | Length of part of plant over the ground (mm) | Hypocotyl elongation ratio (based on the control as 100%) | Length of part of plant under the ground (mm) | Root elongation ratio (based on the control as 100%) |
| Control | 8.1 | 100 | 27.4 | 100 |
| 50 seeds | 10.0 | 128 | 65.4 | 239 |
| 100 seeds | 10.6 | 131 | 69.1 | 252 |
| 150 seeds | 9.3 | 115 | 73.6 | 269 |
| 200 seeds | 11.9 | 147 | 67.5 | 248 |
| | | 129% on average | | 251% on average |

*Length is the average of 8 seedings.

TABLE 3

Measurement results of weight increase
(average weight of 8 seedlings) (unit: mg)

|  | Weight of part of plant over the ground | Increace ratio | Weight of part of plant under the ground | Increase ratio |
|---|---|---|---|---|
| Control | 61.1 | 100% | 15.8 | 100% |
| 50 seeds | 142.9 | 234% | 49.9 | 315% |
| 100 seeds | 156.0 | 255% | 51.7 | 327% |
| 150 seeds | 140.4 | 230% | 55.5 | 351% |
| 200 seeds | 175.7 | 288% | 72.8 | 460% |
|  | 252% increase on average | | 363% increase on average | |

FIG. 4 shows the results of 3 days hydroponics of seedlings in water only (control) and those in water containing lepidimoide in an amount derived from 50, 100, 150, and 200 sunflower seeds (from left to right). From the results, a significant growth promotion effect can be seen on the hypocotyls and roots after the third day of hydroponics.

It was confirmed by Table 2 that after the hydroponics of lettuce, lepidimoide elicited 29% augmentation on the average and 47% augmentation at the maximum in the elongation of hypocotyls and 151% augmentation on the average in the elongation of roots. The greater the number of seeds used for extraction (i.e. the higher the concentration of lepidimoide), the higher the elongation rate was observed. As can be seen from Table 3, lepidimoide elicited 252% augmentation on the average (approx. 2.5 times) and 288% augmentation at the maximum (approx. 2.9 times) in the weight of hypocotyls. Furthermore, there were observed 363% augmentation on the average (approx. 3.6 times) and 460% augmentation (approx. 4.6 times) at the maximum in the weight of roots, so that lepidimoide proved to exhibit a significant promotion effect on an increase in weight. It became evident within the concentration range of lepidimoide tested that the higher the concentration of lepidimoide added, the higher the effect on an increase in the weight of both hypocotyls and roots.

(2) Pea hydroponics

According to the method as described above, a hydroponics test was conducted in the same manner as for lettuce, using 4 secretion solutions containing lepidimoide at a predetermined concentration, and the growth promotion effect was examined after 7 days culture.

Figure 5:
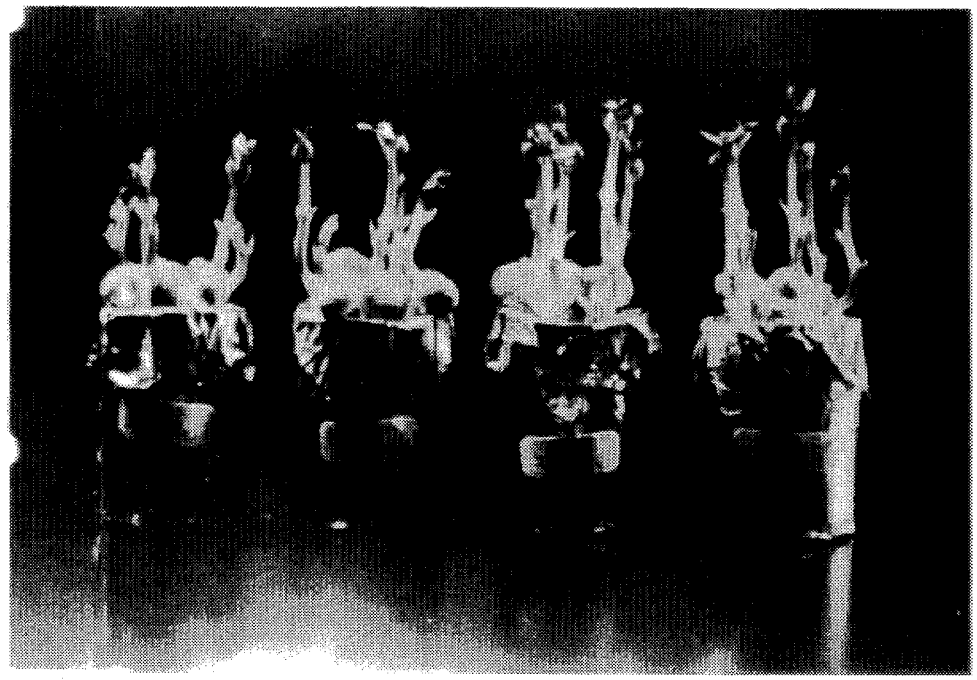
FIG. 5 is a photograph of peas after hydroponics using the present compound.

The results are shown in Tables 4 and 5 and FIG. 5.

TABLE 4

Measurement results of hypocotyl and root weights
(average of 4 seedlings) (after 7 days)

|  | Weight of part of plant over the ground | Weight-increase ratio in part of plant over the ground | Weight of part of plant under the ground | Weight-increase ratio in part of plant under the ground |
|---|---|---|---|---|
| Control | 602.3 | 100% | 679.7 | 100% |
| 50 seeds | 724.9 | 120% | 1067.4 | 157% |
| 100 seeds | 802.7 | 133% | 1175.9 | 173% |
| 150 seeds | 863.7 | 143% | 1078.6 | 159% |
| 200 seeds | 1033.9 | 172% | 1208.3 | 178% |
|  | 142% increase on average | | 167% increase on average | |

TABLE 5

Measurement results of hypocotyl and root lengths
(average weight of 4 seedlings) (after 7 days)

|  | Length of part of plant over the ground | Elongation ratio | Length of part of plant under the ground | Elongation ratio |
|---|---|---|---|---|
| Control | 41.3 | 100% | 51.5 | 100% |
| 50 seeds | 47.3 | 115% | 55.8 | 108% |
| 100 seeds | 59.5 | 144% | 65.8 | 128% |
| 150 seeds | 60.0 | 145% | 72.3 | 140% |
| 200 seeds | 74.5 | 180% | 85.3 | 146% |
|  | 146% increase on average | | 131% increase on average | |

FIG. 5 is a photograph of seedlings after 3 days hydroponics. It is understood that the growth of 3 seedlings (from the right) cultured in the presence of lepidimoide at the same concentrations as in FIG. 4 is promoted as compared with the control (left).

When cultured in water containing lepidimoide (i.e., a sunflower secretion solution), the elongation of pea hypocotyls was approx. 1.5 times on the average and 1.8 times at the maximum as high as that of the control, and the elongation of pea roots was approx. 1.3 times on the average and 1.5 times at the maximum as high as that of the control, as can been seen from Table 4. In addition, the weight increase of pea hypocotyls was approx. 1.4 times on the average and 1.7 times at the maximum as much as that of the control, and the weight increase of pea roots was approx. 1.7 times on the average and 1.8 times at the maximum as much as that of the control. Particularly within the concentration range of lepidimoide tested, it was made evident that the higher the concentration of lepidimoide added, the higher the effect on the elongation and weight increase of both hypocotyls and roots. A significant growth promotion effect was observed within the lepidimoide concentration range in this example.

(3) Tomato hydroponics

According to the method as described above, a hydroponics experiment was carried out using water containing lepidimoide (i.e., the sunflower secretion solution) at 3 predetermined concentrations for the examination of growth promotion effect (after 7 days of culture).

Figure 6:
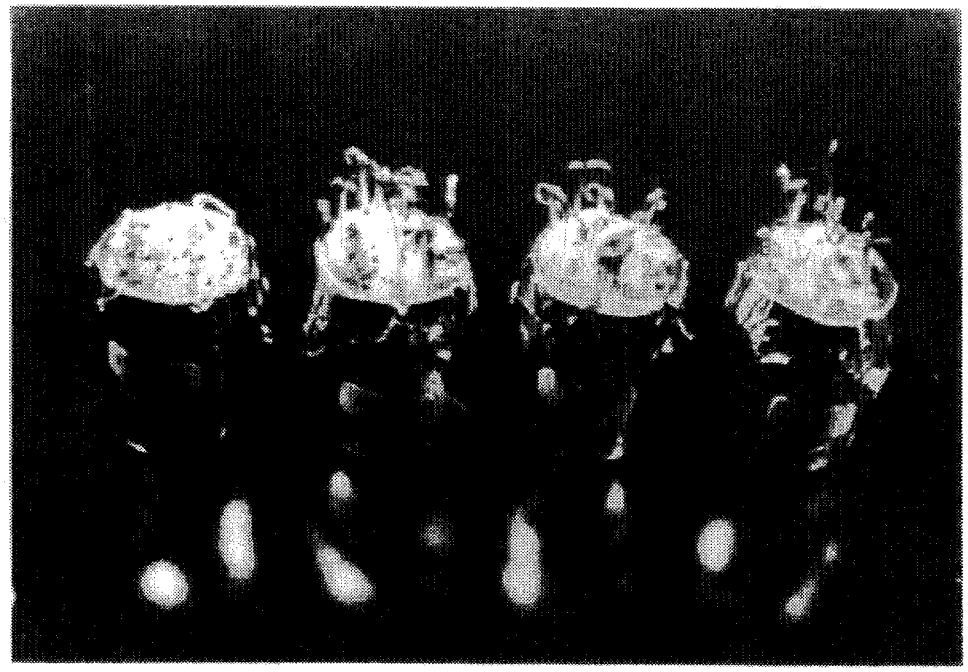
FIG. 6 is a photograph of tomatoes after hydroponics using the present compound.

The results are set forth in Tables 6 and 7 and FIG. 6.

significantly promoted even after 3 days of culture, as shown in FIG. 6.

Figure 7:
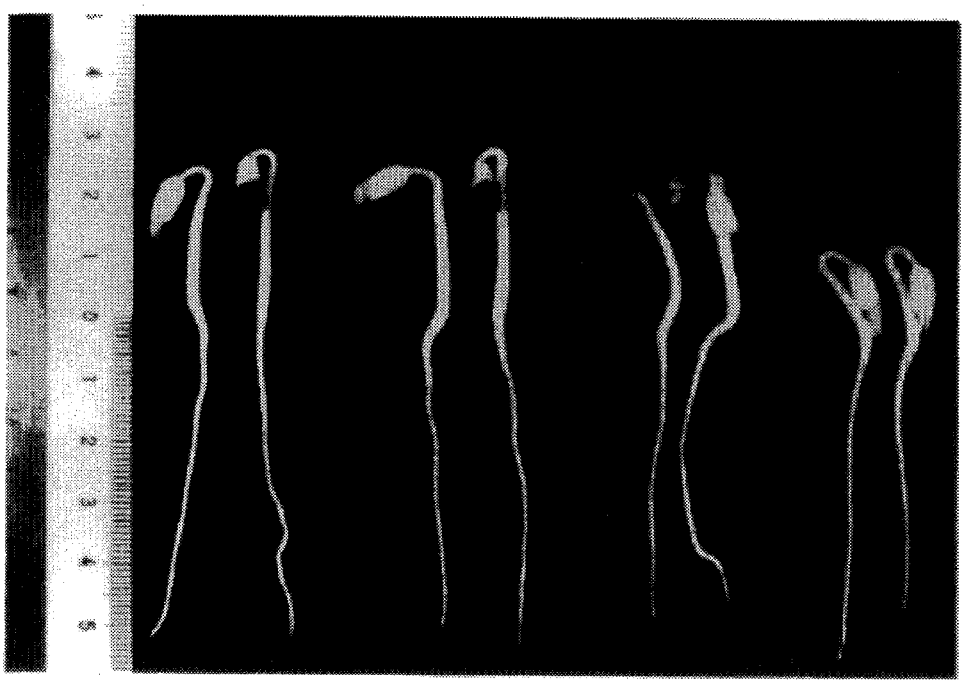
FIG. 7 is a photograph of black matpes after hydroponics using the present compound.

FIGS. 6 and 7 indicate that the presence of lepidimoide was greatly affective for increases in the length and weight of tomato hypocotyls and roots. The hypocotyl and root lengths were approx. 2.2- and 1.4 times respectively at the maximum as long as those of the control. In addition, lepidimoide proved to exhibit a significant effect on increases in hypocotyl and root weights. That is, the hypocotyl and root weights were approx. 1.3- and 3.1 times respectively at the maximum as much as those of the control.

On the other hand, it was found that lepidimoide, at a higher concentration, inhibits root elongation but does not inhibit root weight increase.

(4) Cabbage hydroponics

According to the method as described above, a hydroponics experiment was conducted using water containing lepidimoide (i.e. the sunflower secretion solution) at 3 predetermined concentrations for the examination of growth promotion effect (after 7 days of culture).

The results are set forth in Tables 8 and 9.

TABLE 6

Measurement results of hypocotyl and root lengths
(average of 8 seedlings)

|  | Length of part of plant over the ground (mm) | Elongation ratio (%) | Length of part of plant under the ground (mm) | Elongation ratio (%) |
|---|---|---|---|---|
| Control | 7.9 | 100% | 27.4 | 100% |
| 50 seeds | 17.2 | 218% | 37.9 | 138% |
| 100 seeds | 15.4 | 195% | 17.1 | 62% |
| 200 seeds | 12.7 | 163% | 11.9 | 43% |

TABLE 7

Measurement results of hypocotyl and root weight

|  | Weight of part of plant over the ground (mg) | Increase ratio (%) | Weight of part of plant under the ground (mg) | Increase ratio (%) |
|---|---|---|---|---|
| Control | 6.8 | 100% | 26.4 | 100% |
| 50 seeds | 207.3 | 305% | 88 | 333% |
| 100 seeds | 142.4 | 209% | 26.6 | 101% |
| 200 seeds | 65.9 | 97% | 28.4 | 108% |

As compared with the control (left), the growth of the seedlings incubated in the presence of lepidimoide at the same concentrations as in FIGS. 4 and 5 proved to be

TABLE 8

Measurement result of hypocotyl and root lengths
(average of 8 seedlings)

|  | Length of part of plant over the ground (mm) | Elongation ratio (%) | Length of part of plant under the ground (mm) | Elongation ratio (%) |
|---|---|---|---|---|
| Control | 14.0 | 100% | 15.1 | 100% |
| 50 seeds | 30.8 | 220% | 28.5 | 189% |
| 100 seeds | 25.6 | 183% | 16.3 | 108% |
| 200 seeds | 24.1 | 172% | 14.3 | 75% |

TABLE 9

| | Measurement results of hypocotyl and root weights (average of 8 seedlings) | | | |
|---|---|---|---|---|
| | Weight of part of plant over the ground (mg) | Increase ratio (%) | Weight of part of plant under the ground (mg) | Increase ratio (%) |
| Control | 50.0 | 100% | 367.6 | 100% |
| 50 seeds | 102.7 | 206% | 444.2 | 122% |
| 100 seeds | 55.8 | 112% | 288.9 | 79% |
| 200 seeds | — | — | 232.7 | 63% |

From Tables 8 and 9, it was confirmed that as a result of the growth promotion effect of lepidimoide, cabbage hypocotyl and root elongations were approx. 2.2- and 1.9 times respectively at the maximum as high as those of the control, and the cabbage hypocotyl and root weights were approx. 2- and 1.2 times respectively at the maximum as those of the control.

In summary, it was confirmed that a method for hydroponics using lepidimoide (or a lepidimoide-containing secretion solution from sunflower seeds) is considerably effective for the elongation and weight increase of lettuce, pea, tomato, and cabbage hypocotyls and roots.

It was proved by the above data that lepidimoide applied to hydroponics brings about the significant growth promotion of plants, resulting in a reduction in a period of time required for culture as well as an improvement in growth rate.

Hence, plant growth can be greatly improved according to hydroponics using lepidimoide.

(Example 5)

Growth inhibition of black matpe roots

Sunflower seeds were used for the preparation of a lepidimoide-containing stock solution. According to the method as described in Example 2, a stock solution was prepared by extraction of 2000 sunflower seeds with 2 l water, and it was used as a standard stock solution to be concentrated or diluted as necessary.

One type of moyashi seeds, black seeds (black matpe), was used as a subject plant in an experiment of root growth inhibition using lepidimoide at a concentration expressed in terms of the number of sunflower seeds (0 [control], 150, 500, and 1500 seeds).

500 ml black matpe seeds were immersed at 40° C. for 4 hours in 3 l of an aqueous 20 ppm sodium hypochlorite solution containing lepidimoide. The seeds were then transferred to a plastic vessel of specific volume and grown at 25° C. for 3 days in the dark. During culture, water at 15° C. was spread intermittently at an interval of 8 hours.

FIG. 7 shows the results of the growth inhibition experiment in which lepidimoide was used at a concentration of 0 (control), 150, 500, and 1500 sunflower seeds (from left to right). As is evident from this photograph, the growth inhibition of roots is observed to increase from left to right. In particular, the growth inhibition of roots is significant in the case of 1500 seeds at the right, and their root length was found to be approx. 20% shorter than that of the control.

The growth inhibition effect of lepidimoide on moyashi roots was confirmed from the above results.

(Example 6)

Growth inhibition effect of lepidimoide on black matpe and green gram roots under different treatment conditions Since the growth inhibition effect of lepidimoide on roots was confirmed in Example 5, optimum conditions etc. for lepidimoide treatment were determined under similar experimental conditions, and black matpe and green gram roots were examined for growth inhibitory effect. Culture was continued for 5 days, and the concentration of lepidimoide was approx. twice as high as that in Example 5. The experiment comprises 5 treatments: Treatment 1 involves immersion in a lepidimoide solution every day; treatment 2 immersion on the first day only; treatment 3 immersion on the first and second days; treatment 4 immersion on the first and third days; and treatment 5 immersion on the first and fourth days. On the fifth day, 30 moyashi were arbitrarily picked up from each of the treatment groups, and their hypocotyl and root lengths on the average were determined and compared. The results are set forth in Tables 10 and 11.

TABLE 10

| | Growth inhibition effect on black matpe roots | | | | | |
|---|---|---|---|---|---|---|
| | Control | Treatment 1 | Treatment 2 | Treatment 3 | Treatment 4 | Treatment 5 |
| Hypocotyls | 51.4 | 51.5 | 49.0 | 47.3 | 47.0 | 50.0 |
| Roots | 20.6 | 17.9 | 14.9 | 23.5 | 20.7 | 20.6 |

TABLE 11

| | Control | Treatment 1 | Treatment 2 | Treatment 3 | Treatment 4 | Treatment 5 |
|---|---|---|---|---|---|---|
| Growth inhibition effect on green gram roots | | | | | | |
| Hypocotyls | 43.9 | 46.8 | 43.1 | 45.2 | 48.2 | 49.0 |
| Roots | 30.6 | 17.5 | 16.8 | 21.7 | 19.2 | 16.3 |

From the experimental results in Table 10, it was reconfirmed that lepidimoide treatment is effective for the growth inhibition of black matpe roots. Lepidimoide treatment every day or on the first day was effective, as can be seen from Table 10. Treatment 2 is a simple and economical method since immersion suffices only 1 time and 28% inhibitory effect at the maximum on root growth was achieved.

From the experimental results in Table 11, treatments 1 to 5 proved to be effective for the growth inhibition of green gram roots, and the growth inhibition of roots by lepidimoide proved to be effective particularly for green gram. In addition, 47% inhibition effect at the maximum was observed. 45% inhibition effect was observed even in treatment 2 where immersion was carried out only 1 time, so that treatment 2 is understood to be a most reasonable and economical treatment.

In the case of green gram, the effect on hypocotyl elongation (i.e. the physiological effect of lepidimoide as described hereinbefore) was also observed to some extent.

From the above experiments using black matpe and green gram, it was found that lepidimoide can be used to inhibit the growth of moyashi roots, and it is effective and reasonable to treat moyashi with lepidimoide at the first stage of growth. In this case, treatment 2, where immersion suffices only one time, proved to be economical and suitable for application to the actual production process.

(Example 7)

Growth promotion of moyashi by lepidimoide

As described above, lepidimoide proved to have an effect on hypocotyl elongation, and as shown in data of Example 6, it was expected that lepidimoide is effective for the growth promotion of green gram. Hence, the growth promotion effect of lepidimoide on green gram was evaluated under the same conditions as in Example 5. The concentration of lepidimoide was 1000 sunflower seeds/l, and green gram was cultured for 7 days.

Figure 8:
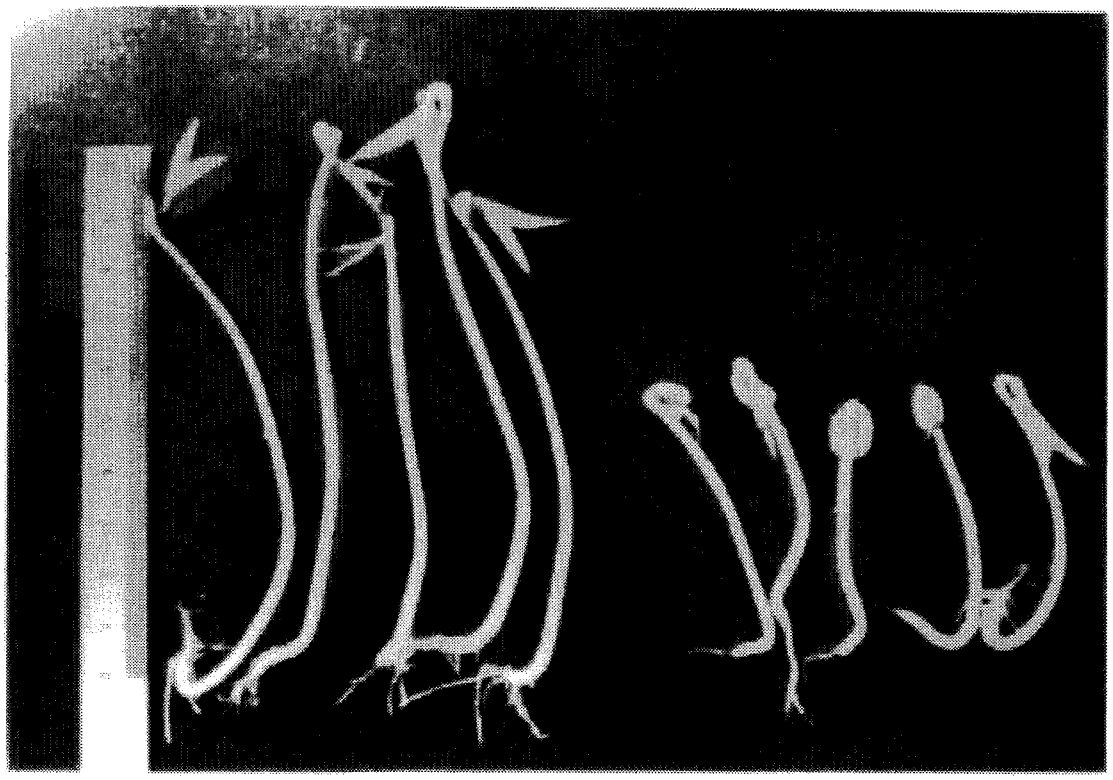
FIG. 8 is a photograph of green gram hypocotyls whose growth was promoted by the present compound.

The results are set forth in FIG. 8. The left seedlings were treated with lepidimoide, and the right seedlings (control) were not treated. It is confirmed by this photograph that the seedlings treated with lepidimoide (left) are approx. twice as large as the untreated seedlings (right). This results indicate the significant growth promotion effect of lepidimoide.

From the above experiments, the significant growth promotion effect brought about by treatment with lepidimoide is expected to significantly improve moyashi production rate and productivity, resulting in a reduction in production costs, and lepidimoide treatment is extremely useful for the large scale production of moyashi.

(Synthesis Example 1)

Benzylation of α-L-rhamnose

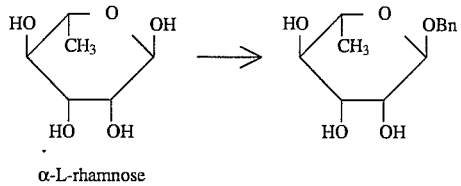

α-L-rhamnose 100 ml benzene was added to 4 g of α-L-rhamnose monohydrate in 20 ml benzyl alcohol, and the mixture was heated for 2 hours under reflux in the presence of a catalytic amount of sulfuric acid (20 drops from a Pasteur pipette), and the resulting water was azeotropically removed. The reaction solution was concentrated under reduced pressure (approx. 40° C.) and purified by column chromatography on silica gel (50 g silica gel, chloroform: methanol=20:1), whereby benzyl glycoside, 3.7 g, was obtained (yield: 93%).

(Synthesis Example 2)

Synthesis of compound (2)

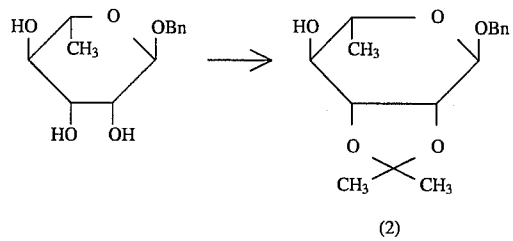

(2)

5.5 g of the benzyl glycoside obtained in Synthesis Example 1 and 10 ml of 2,2-dimethoxypropane were added to 90 ml acetone and allowed to react for 1.5 hours at room temperature in the presence of 2.0 g of p-toluenesulfonic acid as a catalyst. The reaction solution was concentrated under reduced pressure, followed by addition of 100 ml ethyl acetate. Subsequently, the sample was washed with an aqueous, saturated sodium hydrogen carbonate solution (50 ml), then water (50 ml×2), and an aqueous, saturated sodium chloride solution (50 ml), and the product was then dried over sodium sulfate arthydride, concentrated, and purified by column chromatography on silica gel (50 g silica gel, chloroform: methanol=50:1), whereby acetonide (2), 4.9 g, was obtained (yield: 89%).

(Synthesis Example 3)

Synthesis of compound (3)

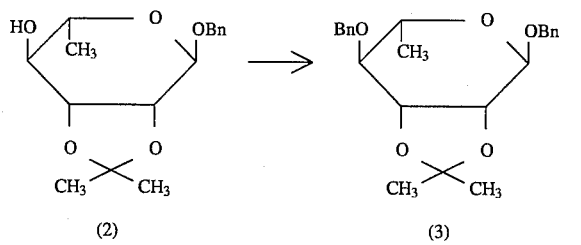

15 ml N,N-dimethylformamide (DMF) containing 4 g of the alcohol derivative (2) obtained in Synthesis Example 2 was added to 10 ml suspension of 0.82 g sodium hydride in DMF, and the mixture was stirred at 0° C. for 5 minutes and at room temperature for 45 minutes. The reaction solution was cooled to 0° C. again, followed by addition of 3.4 ml benzyl bromide. The mixture was stirred at 0° C. for 40 minutes and at room temperature for 39 hours. To the reaction solution (0° C.) were added 0.5 ml methanol and then 50 ml water, and the product was extracted with ethyl acetate (200 ml). The organic layer was washed with an aqueous, saturated sodium chloride solution (100 ml×2), then dried over sodium sulfate arthydride, and concentrated. The concentrate was purified by chromatography on silica gel (100 g silica gel, hexane: ethyl acetate=5:1), whereby benzyl derivative (3), 3.4 g, was obtained (yield: 84.2%).

(Synthesis Example 4)

Synthesis of compound (4)

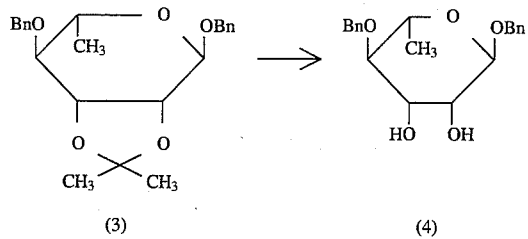

1,4-Dioxane, acetic acid, and water, 30 ml each, were added to 4 g of the benzyl derivative (3) obtained in Synthesis Example (3), and the mixture was allowed to react at 70°–75° C. for 3.5 hours. The reaction solution was poured into 300 ml ethyl acetate, and the organic layer was washed with water (150 ml), an aqueous, saturated sodium hydrogen carbonate solution (100 ml), and an aqueous, saturated sodium chloride solution (200 ml×2), then dried over sodium sulfate arthydride, and concentrated. For purification, the product was fractionated by column chromatography on silica gel (60 g silica gel, hexane: ethyl acetate: 5:1 to 1:1), whereby compound (4), 2.8 g, was obtained (yield: 70%).

(Synthesis Example 5)

Synthesis of compounds (5) and (6)

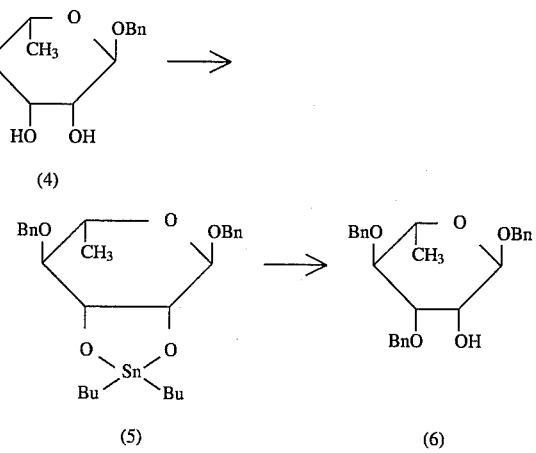

A mixture of 2.24 g of compound (4) obtained in Synthesis Example 4 and 1.82 g dibutyltin oxide ($Bu_2SnO$) in 30 ml abs. benzene was heated over 3 hours under reflux, and the resulting water was azeotropically removed. The reaction solution was concentrated and then dried for 1 hour with a vacuum pump, so that compound (5) was obtained. 1.5 g cesium fluoride (CsF) was added to compound (5) in situ, and the sample was then dried for another 1 hour with a vacuum pump, followed by addition of 30 ml DMF and then 3 ml benzyl bromide. The mixture was allowed to react for 1.5 hours, and then the reaction solution was poured into 100 ml ethyl acetate. The organic layer was washed with water (100 ml×2) and then with an aqueous, saturated sodium chloride solution (100 ml), and the solution was dried over sodium sulfate arthydride and concentrated. For purification, the product was fractionated by column chromatography on silica gel (90 g silica gel, hexane: ethyl acetate=5:1 to 2:1), whereby compound (6), 2 g, was obtained (yield in the 2-step reaction: 88%).

(Example 8)

Synthesis of compound (7)

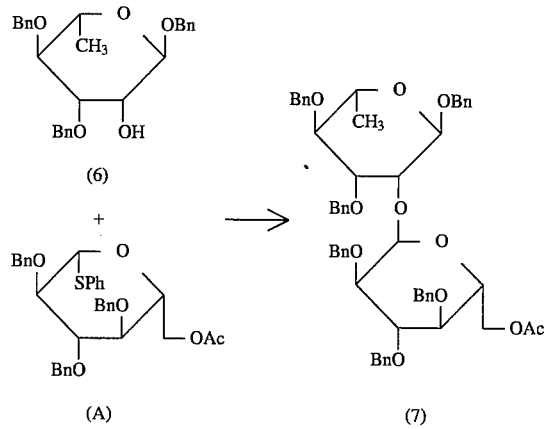

6 g molecular sleve 4A was added to a mixture of 600 mg compound (A) and 1114 mg of compound (6) obtained in Synthesis Example 5, and the mixture was dried under reduced pressure with a vacuum pump. 3 hours thereafter, 20 ml abs. dichloromethane was added thereto, followed by 1 hour stirring. Subsequently, 2.5 g methylsulphenylbromide (MSB) in 5 ml 1,2-dichloroethane was added at 0° C. in the dark to the mixture, which in turn was stirred for 1 hour. The reaction temperature was lowered to 0° C., followed by addition of 4 ml triethylamine and then 50 ml ethyl acetate. The reaction solution was filtered, dried over sodium sulfate arthydride, and concentrated. The product was purified by column chromatography on silica gel (160 g silica gel, hexane: ethyl acetate=7:1 to 7:3), whereby compound (7), 1400 mg, was obtained (yield: 37.5%).

Figure 9:
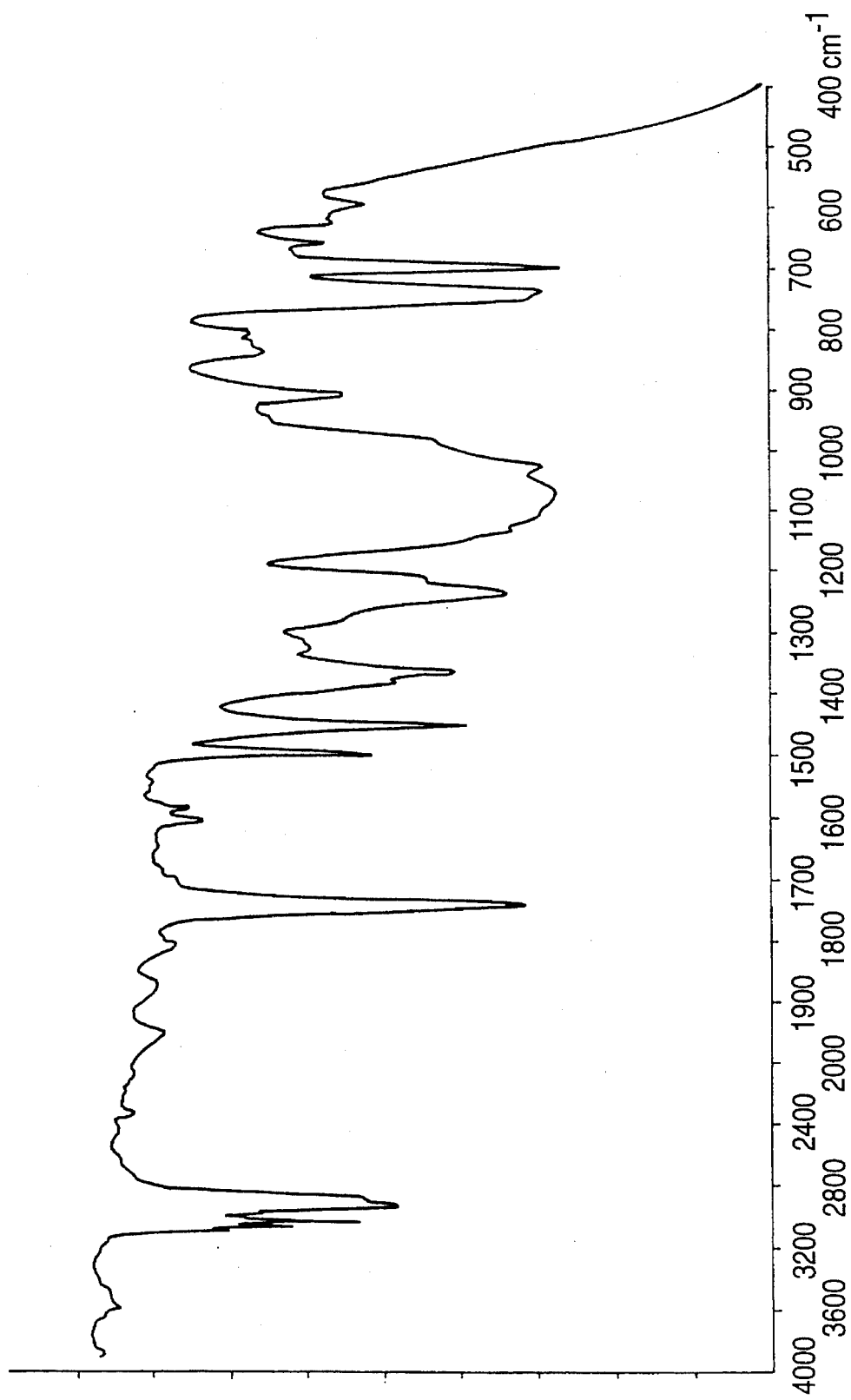
FIGS. 9, 10, and 11 show IR spectrum, $^1$H-NMR spectrum, and $^{13}$C-NMR of compound (7), respectively.

IR spectrum: see FIG. 9.

Figure 10A:
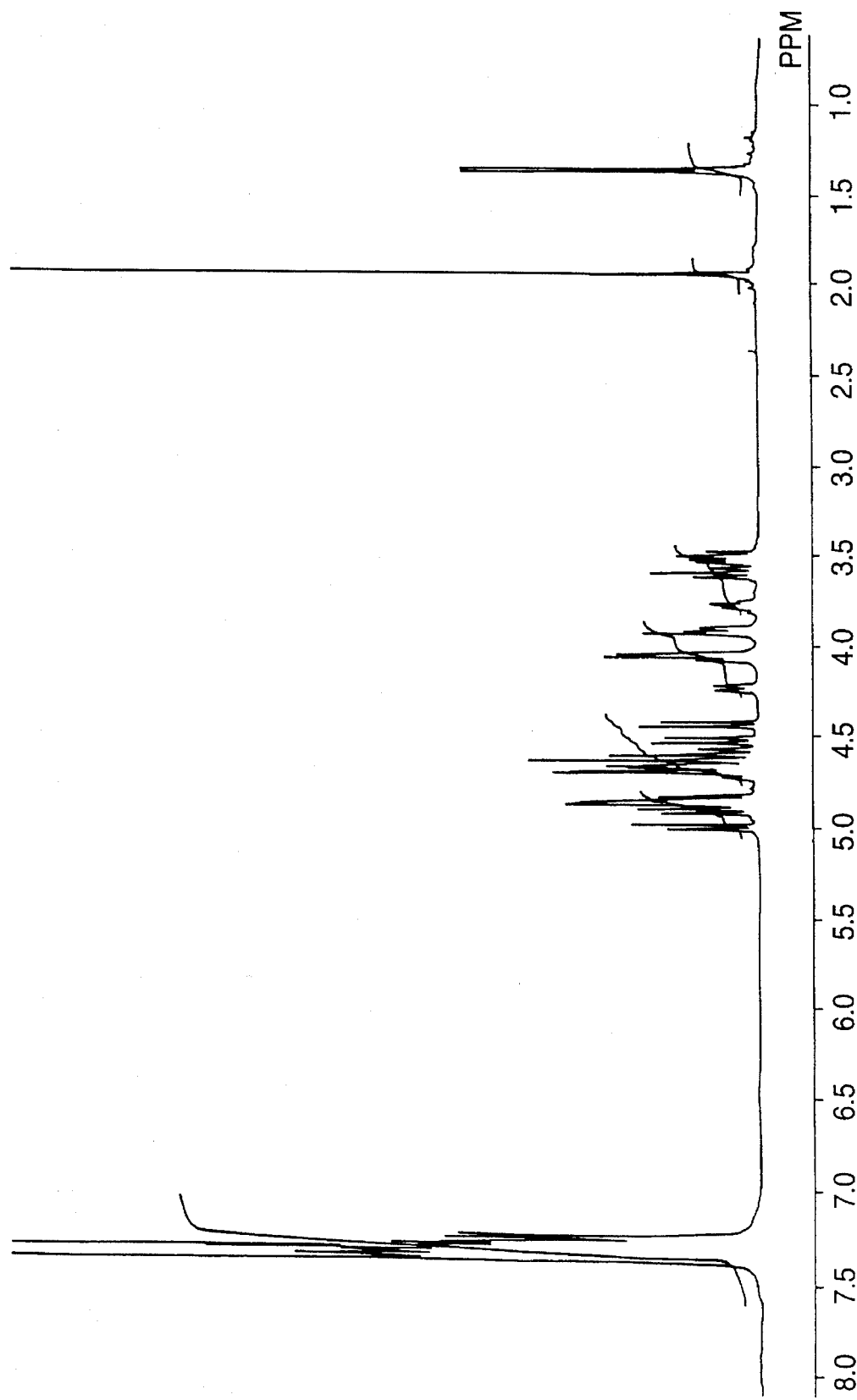
Figure 10B:
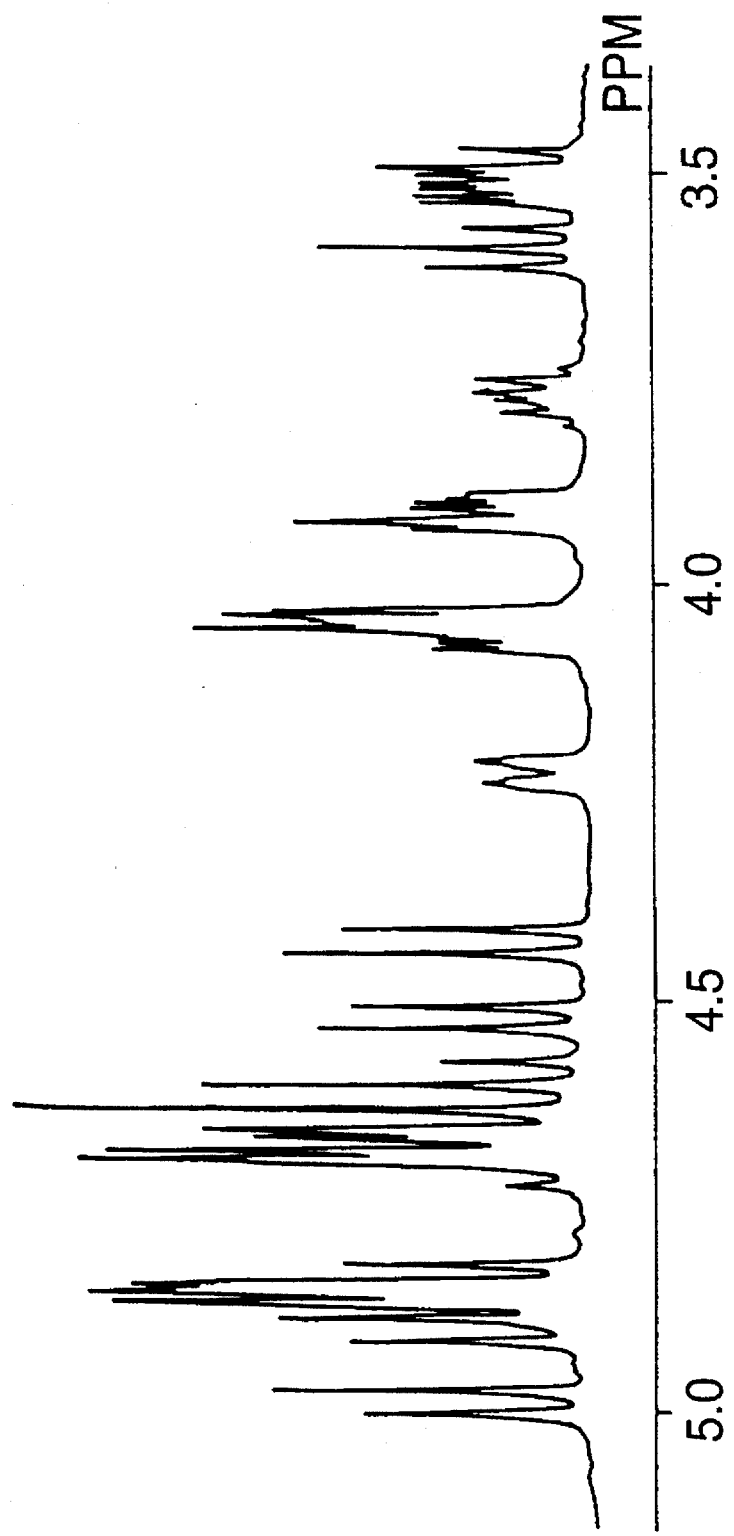

$^1$H-NMR spectrum (CDCl$_3$): see FIG. 10.

Figure 11:
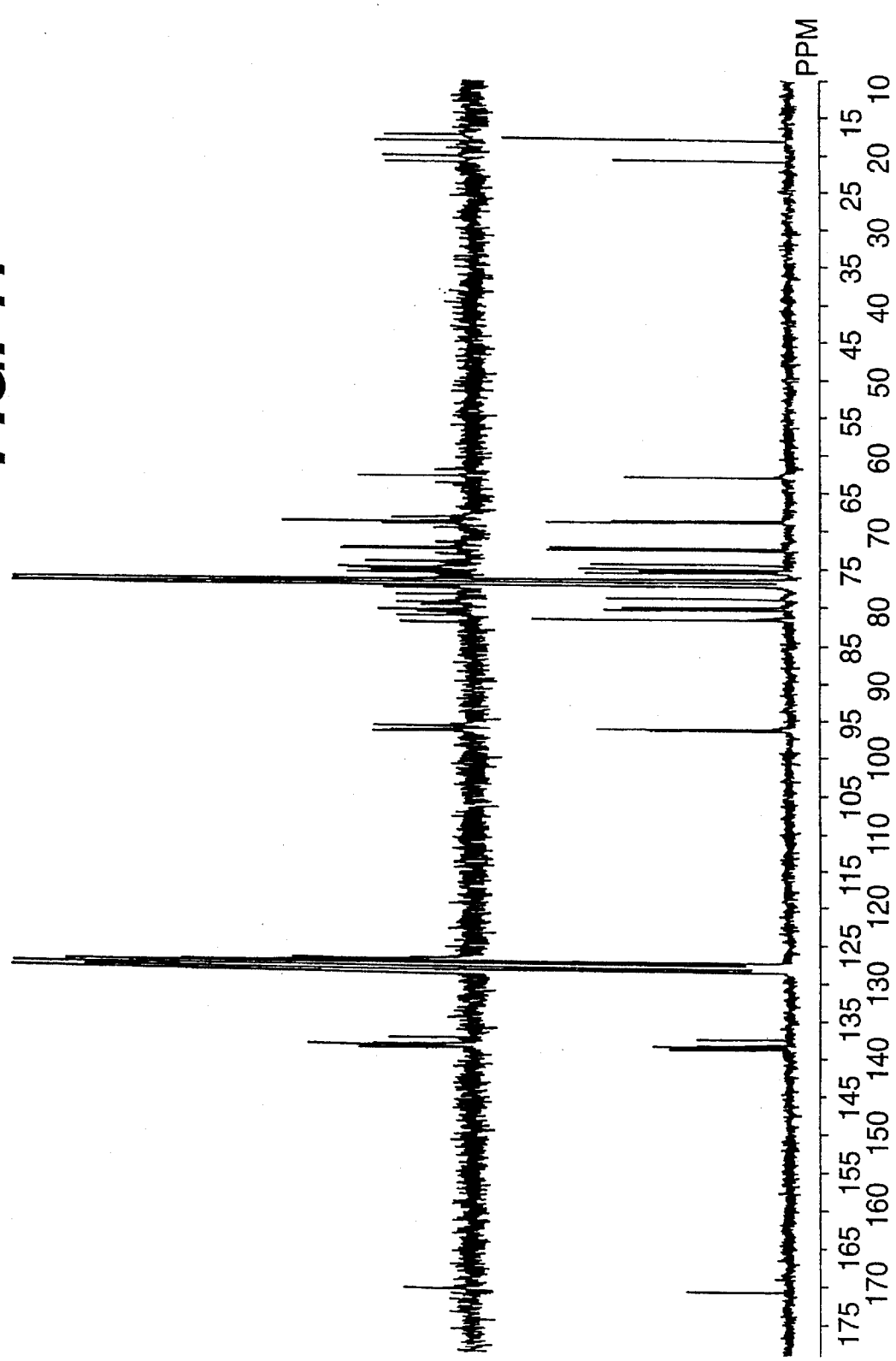

$^{13}$C-NMR spectrum (CDCl$_3$): see FIG. 11.

(Example 9)

Synthesis of compound (8)

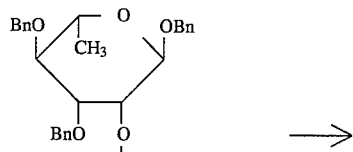

(7)

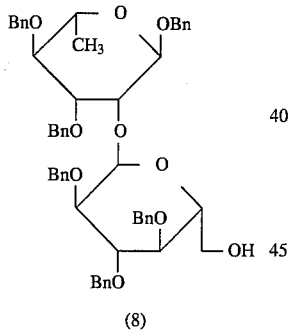

(8)

300 mg of compound (7) obtained in Example 8 was dissolved in 6 ml methanol, and 100 mg potassium carbonate was added thereto, and the mixture was stirred at room temperature for 1 hour and 20 minutes. The reaction solution was poured into ethyl acetate, and the organic layer was washed with an aqueous, saturated sodium chloride solution (40 ml×3), dried over sodium sulfate arkhydride, and concentrated. For purification, the product was separated by thin layer chromatography, whereby compound (8), 285 mg, was obtained (quantitatively).

(Example 10)

Synthesis of compound (8a)

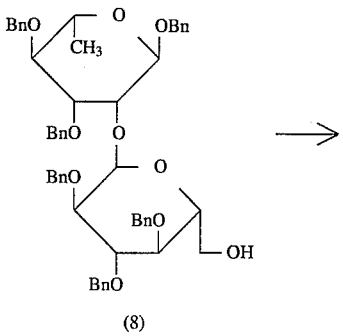

(8)

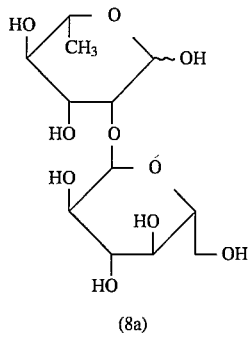

(8a)

10 mg of compound (8) obtained in Example 9 was dissolved in 3 ml methanol. The air in the reaction vessel was degassed and replaced by argon, and 10% palladium-carbon was added at 0° C. thereto, and then the argon in the vessel was replaced by hydrogen at room temperature. The mixture was then stirred for 15 hours at atmospheric pressure. The hydrogen in the vessel was replaced by argon. After addition of Celite, the reaction mixture was filtered. The filtrate was concentrated and then purified by preparative silica gel chromatography (chloroform:methanol=2:1), whereby compound (8a), 9 mg, was obtained (yield: 90%).

Figure 12:
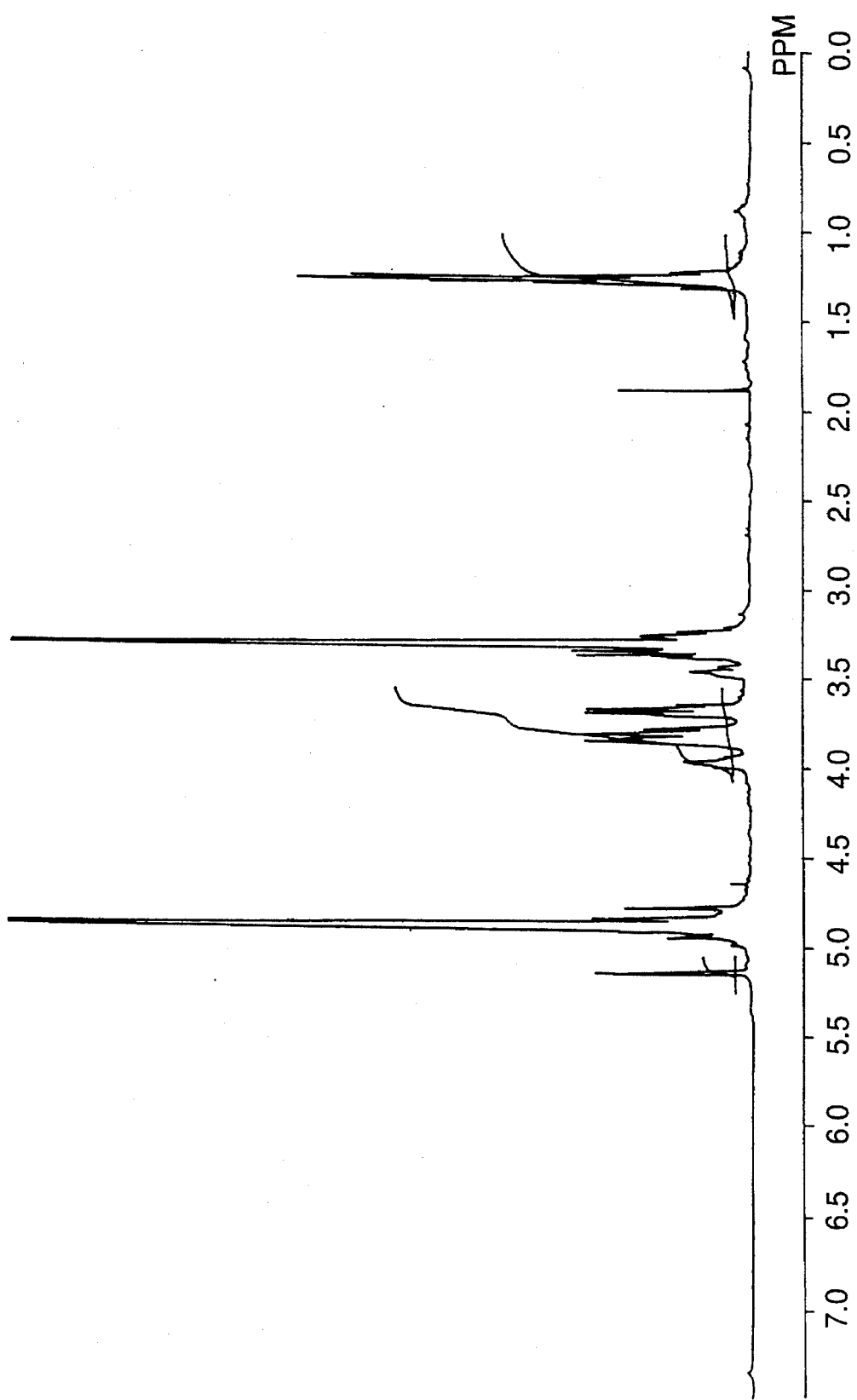
FIG. 12 shows $^1$H-NMR spectrum of compound (8a).

$^1$H-NMR spectrum (CD$_3$OD): see FIG. 12.

(Example 11)

Synthesis of compound (9)

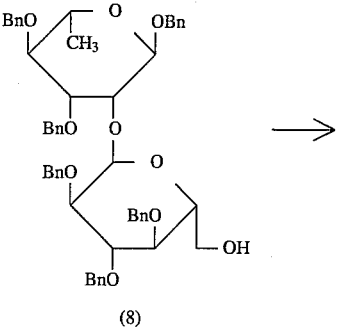

(8)

-continued

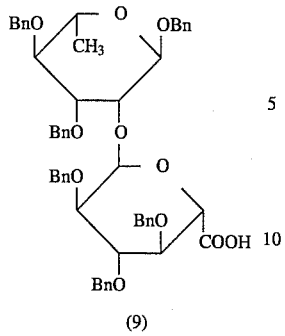

(9)

240 mg of compound (8) obtained in Example 9 was dissolved in a combined solvent of 2 ml DMSO and 0.8 ml triethylamine, and 400 mg SO$_3$-pryridine was added little by tittle. The reaction solution was stirred for 4 hours at room temperature and was then poured into water. After extracted with 30 ml ethyl acetate, the organic layer was washed with an aqueous, saturated sodium chloride solution (15 ml×2), dried over sodium sulfate arthydride, and concentrated.

230 mg of this concentrate, 1 ml of 2-methyl-2-butene, and 50 mg of sodium dihydrogen phosphate were dissolved in a combined solvent of 2 ml water and 3 ml of t-butyl alcohol. 170 mg of sodium chlorite (approx. 85% NaClO$_2$) was added little by little, and then the mixture was then stirred for 2 hours. The reaction solution was cooled to 0° C. and poured into 30 ml ethyl acetate. Subsequently, the solution was made acidic with 1N hydrochloric acid and then washed with an aqueous, saturated sodium chloride solution (20 ml×3), dried over sodium sulfate arthydride, and concentrated. The residue was purified by thin layer chromatography, whereby carboxylic acid (9), 190 mg, was obtained (yield in the two-step reaction: 79%).

(Example 12)

Synthesis of compound (9a)

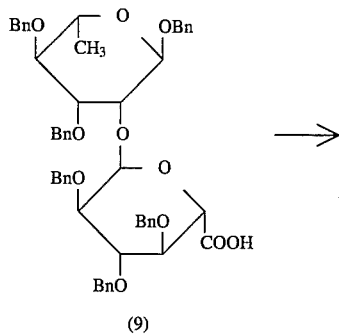

(9)

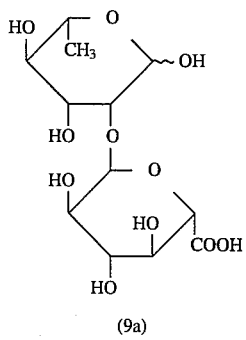

(9a)

20 mg of compound (9) obtained in Example 11 was dissolved in 5 ml methanol. The air in the reaction vessel was degassed and replaced by argon, and 10% palladium-carbon was added at 0° C. thereto, and then the argon in the vessel was replaced by hydrogen at room temperature. The mixture was then stirred for 15 hours at atmospheric pressure.

The hydrogen in the vessel was replaced by argon. After addition of Celite, the reaction mixture was filtered. The filtrate was concentrated and then purified by preparative silica gel chromatography (chloroform:methanol=1:1), whereby compound (9a), 18 mg, was obtained (yield: 90%).

Figure 13:
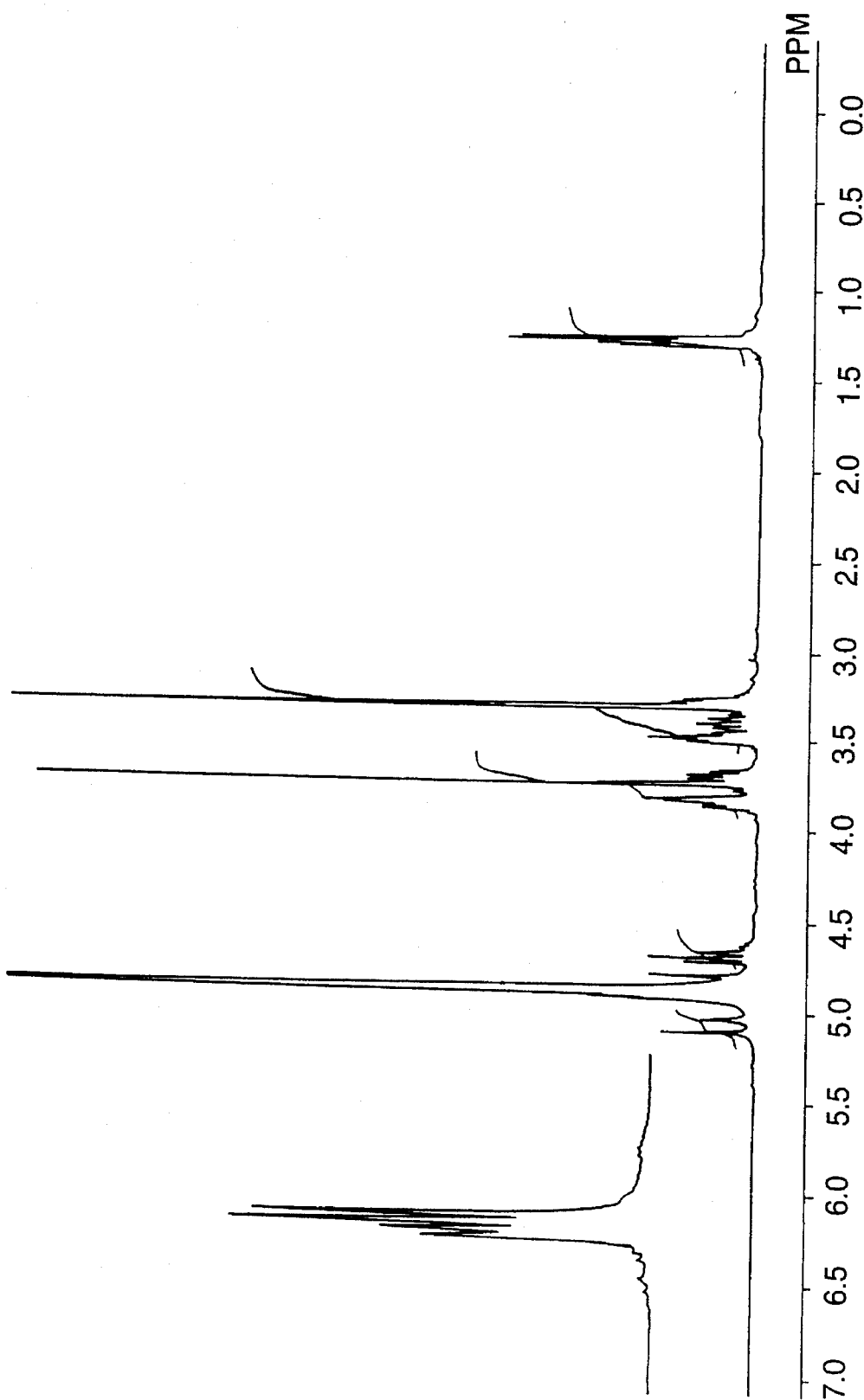
FIG. 13 shows $^1$H-NMR spectrum of compound (9a).

$^1$H-NMR spectrum (CD$_3$OD): see FIG. 13.

(Example 13)

Synthesis of compound (10)

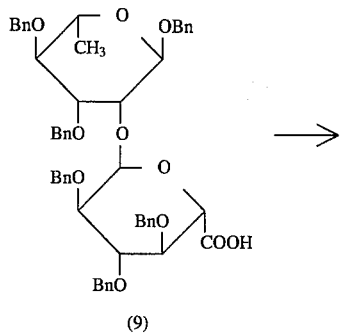

(9)

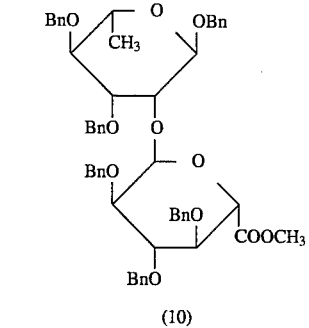

(10)

200 mg of compound (9) obtained in Example 11 was dissolved in a mixture of 5 ml benzene and 1 ml methanol, followed by addition of an excess amount of trimethylsilyldiazometha ne (in 10% benzene). 5 minutes thereafter, the solvent was evaporated, whereby compound (10), 190 mg, was obtained (quantitatively).

(Example 14)

Synthesis of compound (10a)

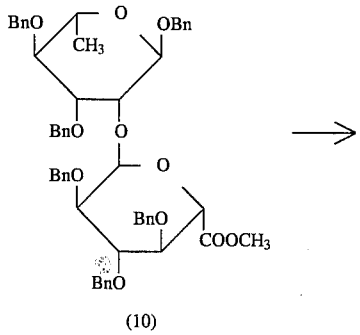

(10)

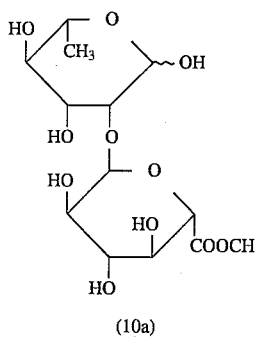

(10a)

174 mg of compound (10) obtained in Example 13 was dissolved in a combined solvent of 10 ml methanol and 10 ml ethyl acetate. The air in the reaction vessel was degassed and replaced by argon, and 10% palladium-carbon was added at 0° C. thereto, followed by replacement at room temperature of the argon by hydrogen. The mixture was then stirred for 15 hours at atmospheric pressure, and the hydrogen in the vessel was replaced by argon. After addition of Celite, the reaction mixture was filtered, and the filtrate was concentrated and purified by preparative chromatography on silica gel (chlorofom: methanol=2:1), whereby alcohol derivative (10 a), 170 mg, was obtained (yield: 98%).

Figure 14:
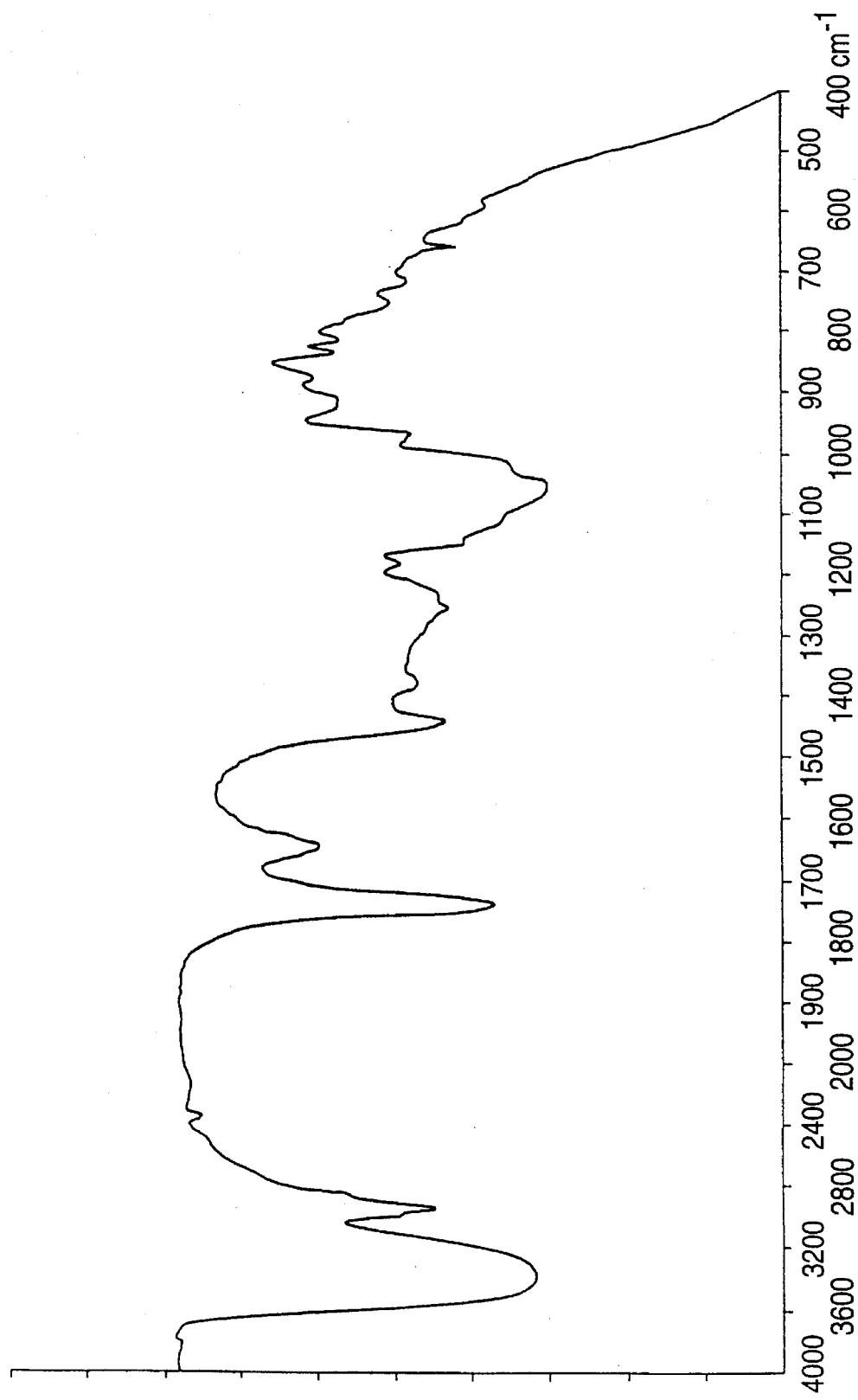
FIGS. 14, 15, and 16 show IR spectrum, $^1$H-NMR spectrum, and $^{13}$C-NMR spectrum of compound (10a), respectively.
Figure 15:
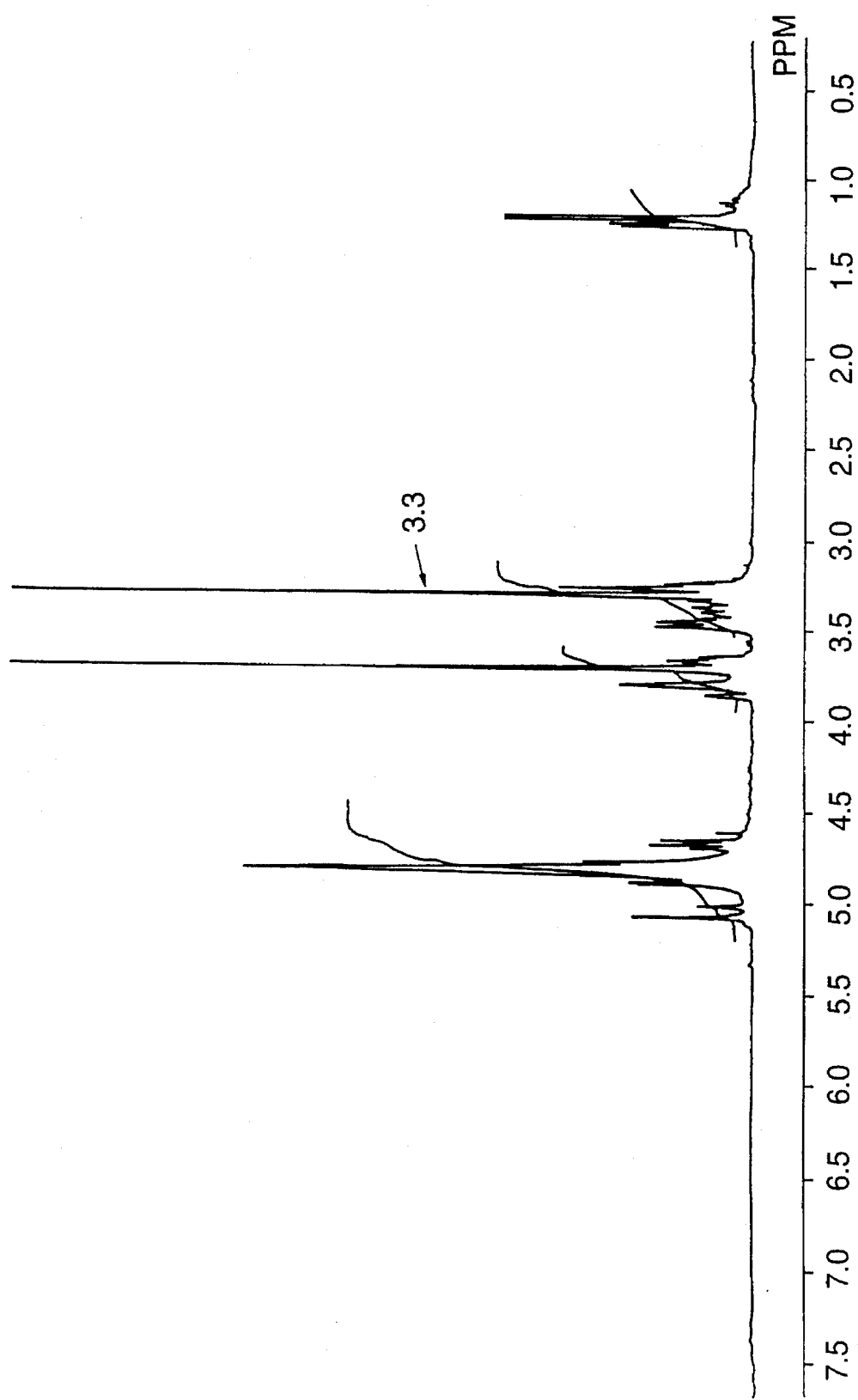
Figure 16:
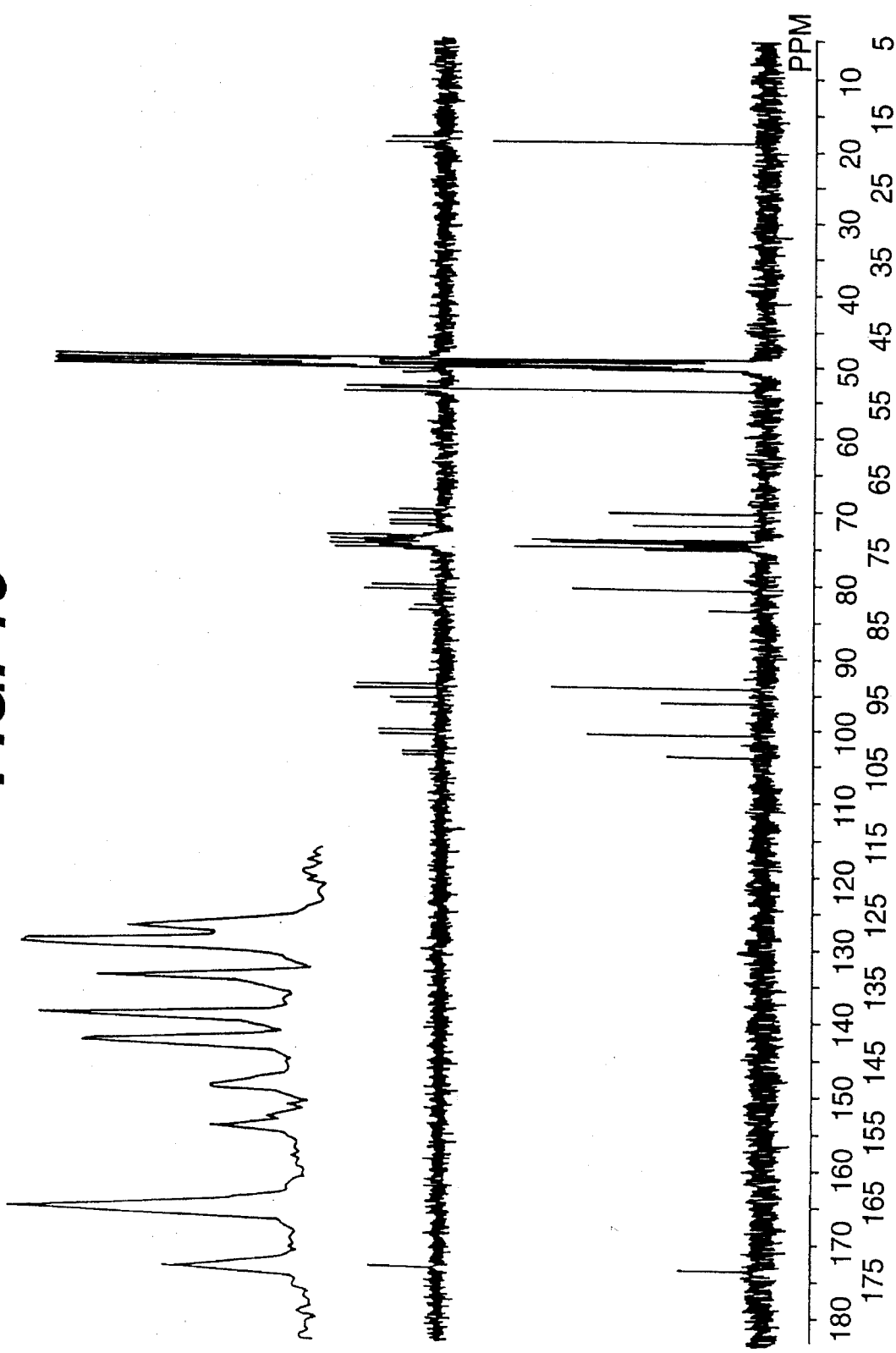

IR spectrum: see FIG. 14.
$^1$H-NMR spectrum (CD$_3$OD): see FIG. 15.
$^{13}$C-NMR spectrum (CD$_3$OD): see FIG. 16.

(Example 15)

Synthesis of compound (11)

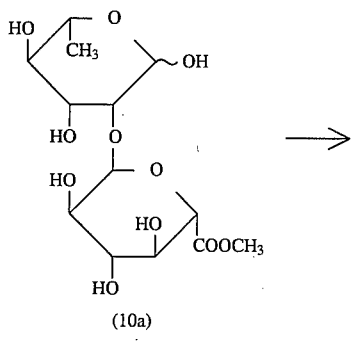

65 mg of the hexalcohol derivative (10a) obtained in Example 14 was dissolved in 0.8 ml pyridine, and 0.5 ml acetic arthydride was added thereto. Then, the mixture was stirred for 11 hours at room temperature. After addition of toluene, the solvent was azeotropically removed, and the residue was purified by preparative chromatography on silica gel (chloroform:acetone=5:1), whereby compound (11), 62 mg, was obtained (quantitatively).

(Example 16)

Synthesis of compounds (12) and (12')

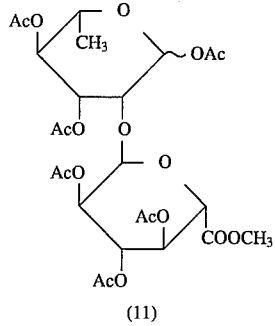

(11)

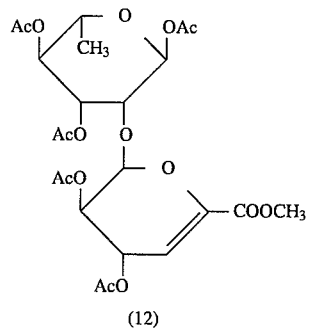

(12)

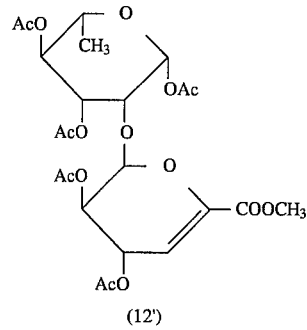

(12')

15 mg of 1,8-diazabicyclo[5.4.0]-7-undecene (DBU) was added to 0.5 ml pyridine containing 1.3 mg of compound (11) obtained in Example (15), and the mixture was stirred under cooling on ice for 1 hour and at room temperature for additional 14 hours.

The reaction solution was poured into 30 ml ethyl acetate and was then washed with 5 ml of 1N hydrochloric acid and then with an aqueous, saturated sodium chloride solution (15 ml×3). The sample was dried over sodium sulfate anhydride and concentrated. The residue was purified on thin layer chromatography, whereby 0.7 mg of compound (12) and 0.6 mg of compound (12') were obtained (yield (12): 54%, (12'): 43%).

Figure 17:
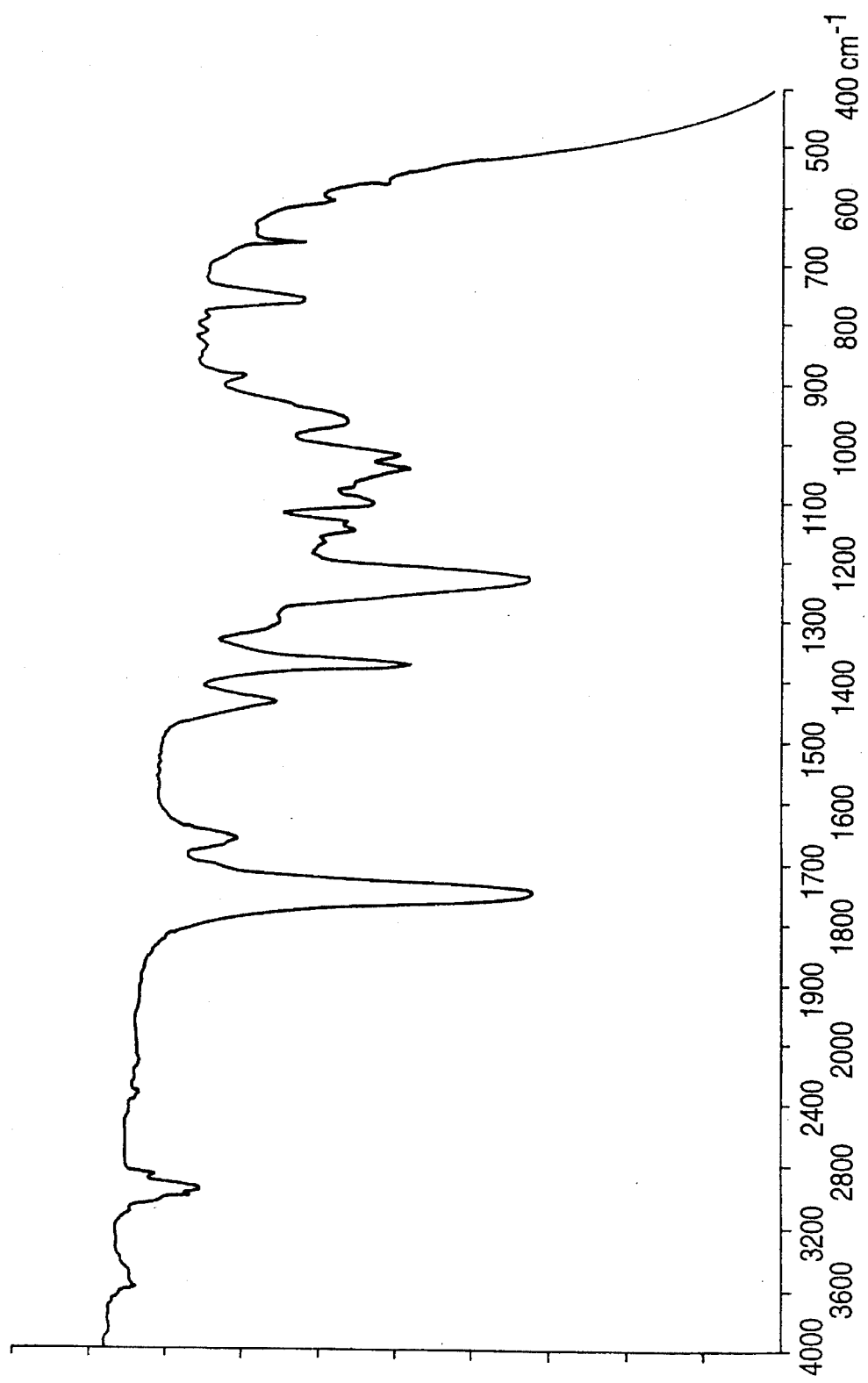
FIGS. 17, 18, and 19 show IR spectrum, $^1$H-NMR spectrum, and $^{13}$C-NMR spectrum of compound (12), respectively.
Figure 18:
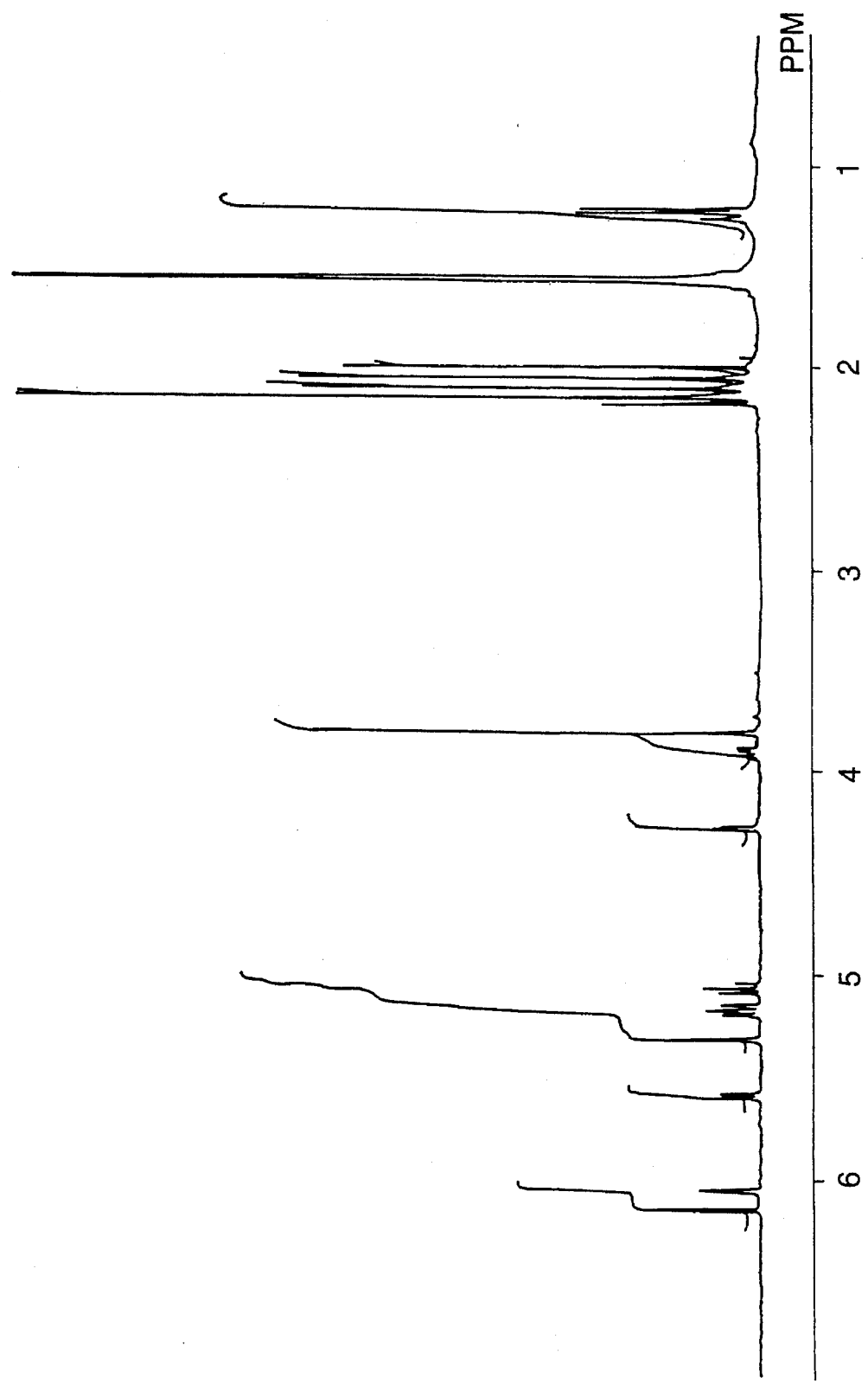

Compound (12):
State: Colorless oil residue
Mass spectrum: m/z 546.1564 (M$^+$)
IR spectrum (film): 1740 cm$^{-1}$(see FIG. 17)
$^1$H-NMR spectrum: δ(CDCl$_3$) (see FIG. 18) 6.14 (1H, d, J=3.3 Hz), 6.04 (1H, d, J=2.0 Hz) 5.59 (1H, dd, J=7.5, 3.3 Hz), 5.31 d, J=2.4 Hz) 5.18 (1H, dd, J=7.5, 2.4 Hz), 5.16 (1H, dd, J=9.8, 3.4 Hz), 5.06 (1H, dd, J=9.8, 9.3 Hz), 4.27 (1H, dd, J=3.4, 2.0 Hz), 3.88 (1H, dq, J=9.3, 6.0 Hz), 3.80

(3H, s), 2.14 (6H, s), 2.10 (3H, s) 2.05 (3H, s), 2.00 (3H, s), 1.22 (3H, d, J=6.0 Hz)

Figure 19:
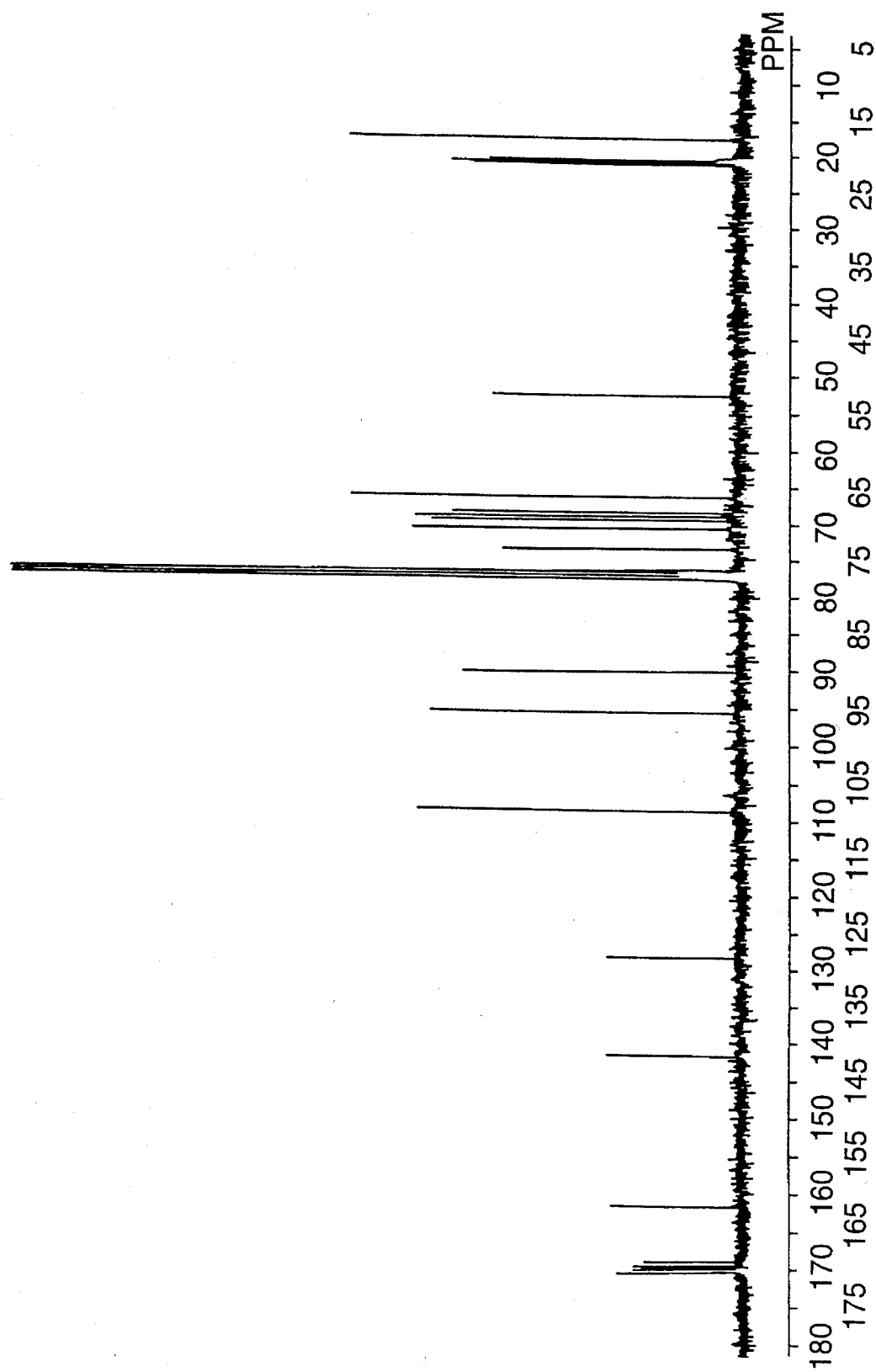

$^{13}$C-NMR spectrum: δ(CDCl$_3$) (see FIG. 19) 170.4(s), 170.1(s), 169,9(s), 169.5(s), 168.8(s), 161.6(s), 141.6(s), 108.6(d), 95.6(d), 90.2(d), 73.3(d), 70.4(d), 69.4(d), 69.0(d), 68.3(d), 66.2(d), 52.5(q), 20.94(q), 20.90(q), 20.7(q), 20.6(q), 20.5(q), 17.5(q)

Figure 20:
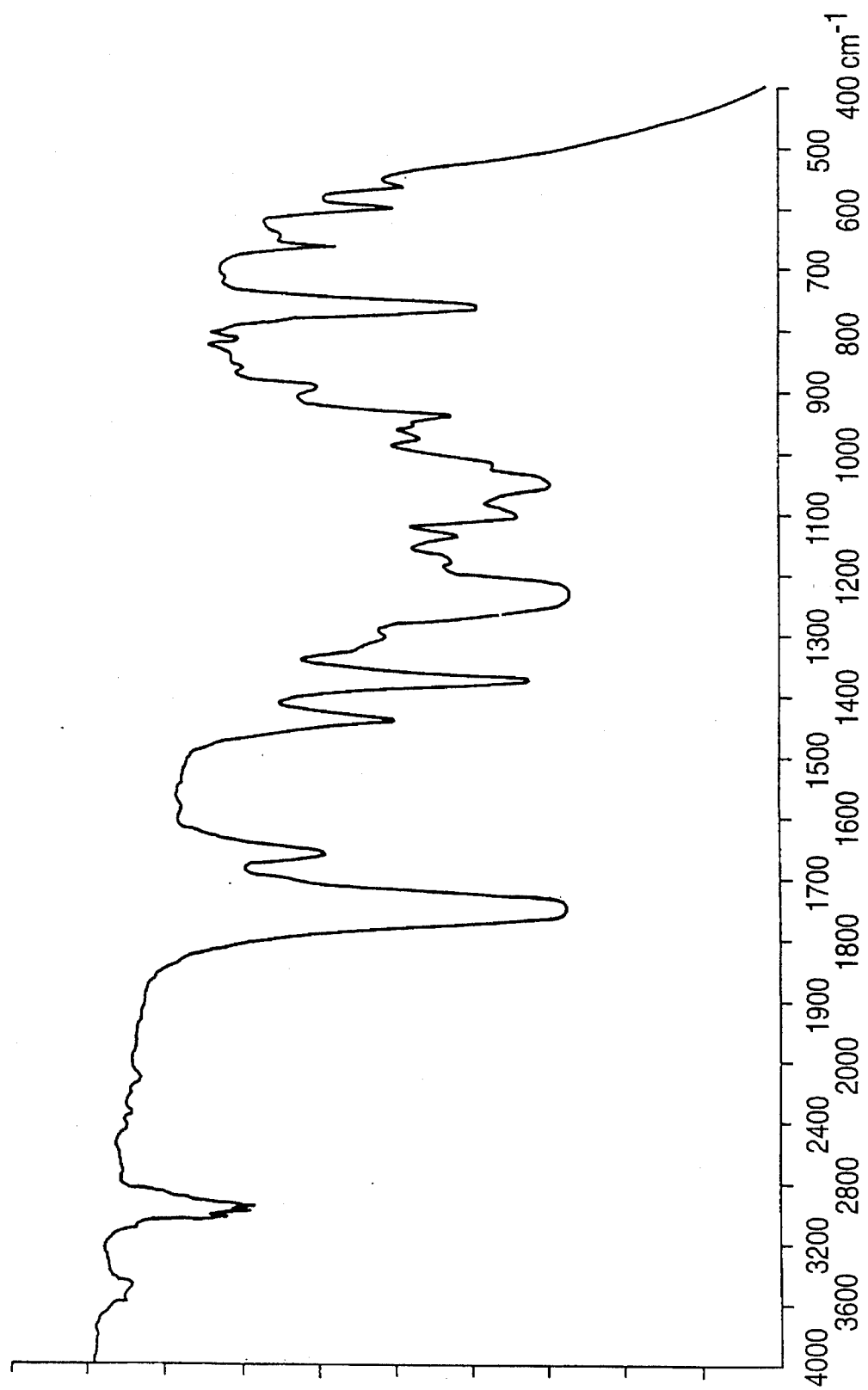
FIGS. 20 and 21 show IR spectrum and $^1$H-NMR spectrum of compound (12'), respectively.
Figure 21:
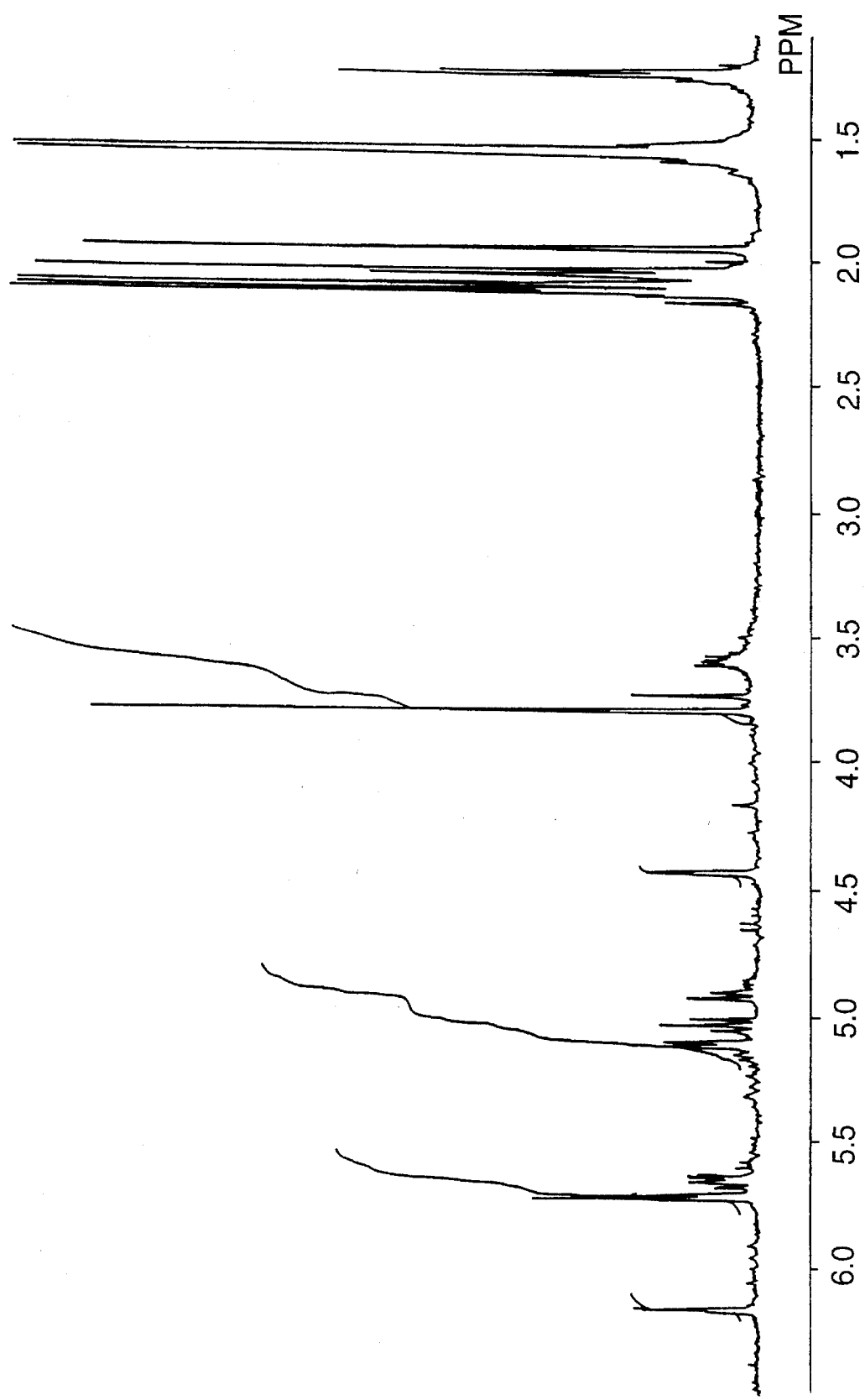

Compound (12'):

State: Colorless oil residue Mass spectrum: m/z 546.1609 (M$^+$) IR spectrum (film): 1740 cm$^{-1}$(see FIG. 20) $^1$H-NMR spectrum: δ(CDCl$_3$) (see FIG. 21) 6.15 (1H, d, J=2.9 Hz), 5.72 (1H, s), 5.71 (1H, d, J=2.9 Hz), 5.64 (1H, dd, J=7.8, 2.9 Hz), 5.10 (1H, dd, J=7.8, 2.9 Hz), 5.02 (1H, dd, J=9.8, 9.8 Hz), 4.91 (1H, dd, J=9.8, 3.2 Hz), 4.43 (1H, d, J=3.2 Hz), 3.59 (1H, dq, J=9.8, 6.1 Hz), 3.80 (3H, s), 2.13 (3H, s), 2.12 (3H, s), 2.10 (3H, s), 2.04 (3H, s), 1.95 (3H, s), 1.25 (3H, d, J=6.1 Hz)

(Example 17)

Synthesis of compound (1)

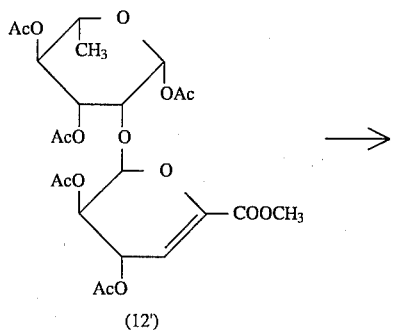

(1)

3.1 mg of compound (12') obtained in Example 16 was dissolved in a combined solvent of 1 ml water and 1 ml methanol, followed by addition of 0.034 ml of 50% methanol (aq.) containing 6N sodium hydroxide. The mixture was stirred for 20 minutes, and the reaction solution was concentrated and was then purified by preparative chromatography on silica gel, whereby lepidimoide (1), 2.1 mg, was obtained (quantitatively).

FAB (H$_2$O +G) HRFABMS
C$_{12}$H$_{17}$O$_{10}$Na$_2$ 367.0591 M+Na
[α]$_D^{21}$+65.2° (C 0.025, D$_2$O) Synthetic product
$^1$R spectrum: 3,300, 1590 cm$^{-1}$
$^1$H-NMR spectrum: δ(D$_2$O) 5.72 (1H, d, J=3.2 Hz), 5.17 (1H, d, J=1.6 Hz), 5.07 (1H, d, J=2.3 Hz), 4.26 (1H, dd, J=6.9, 3.2 Hz), 4.08 (1H, dd, J=3.4, 1.6 Hz), 3.79 (1H, dq, J=9.7, 6.8 Hz), 3.76 (1H, dd, J=9.7, 3.4 Hz), 3.72 (1H, dd, J=6.9, 2.3 Hz), 3.31 (1H, dd, J=9.7, 9.7 Hz), 1.80 (3H, d, J=6.8 Hz)

(Example 18)

Synthesis of compound (13)

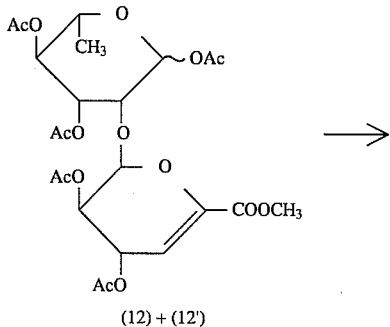

(12) + (12')

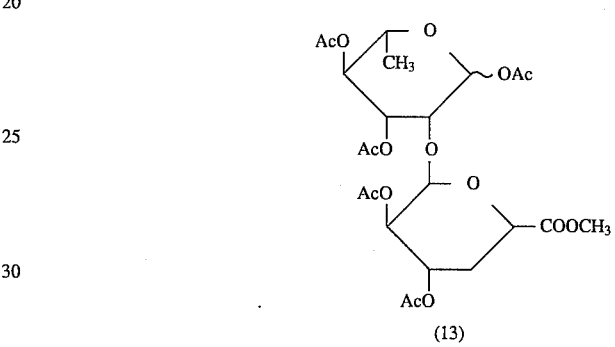

(13)

3.3 mg in total of compounds (12) and (12') obtained in Example 16 were dissolved in 4 ml methanol. The air in the reaction vessel was degassed and replaced by argon, and 10% palladium-carbon was added at 0° C., and then the argon in the vessel was replaced at room temperature by hydrogem The mixture was then stirred for 15 hours at atmospheric pressure. The hydrogen in the vessel was replaced by argom After addition of Celite, the reaction mixture was filtered. The filtrate was concentrated and then purified by preparative silica gel chromatography (chloroform: methanol=50:1), whereby compound (13), 2.9 mg, was obtained (yield 88%).

(Example 19)

Synthesis of compound (14)

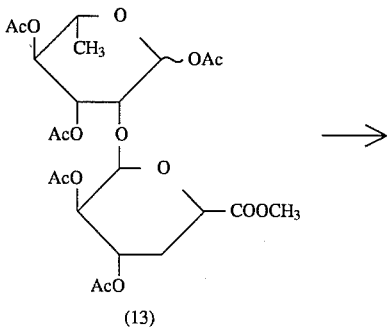

(13)

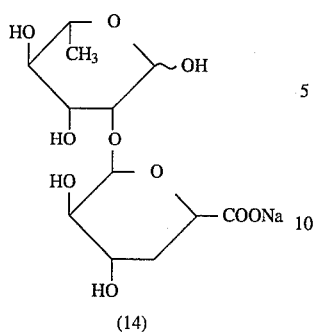

(14)

Figure 22:
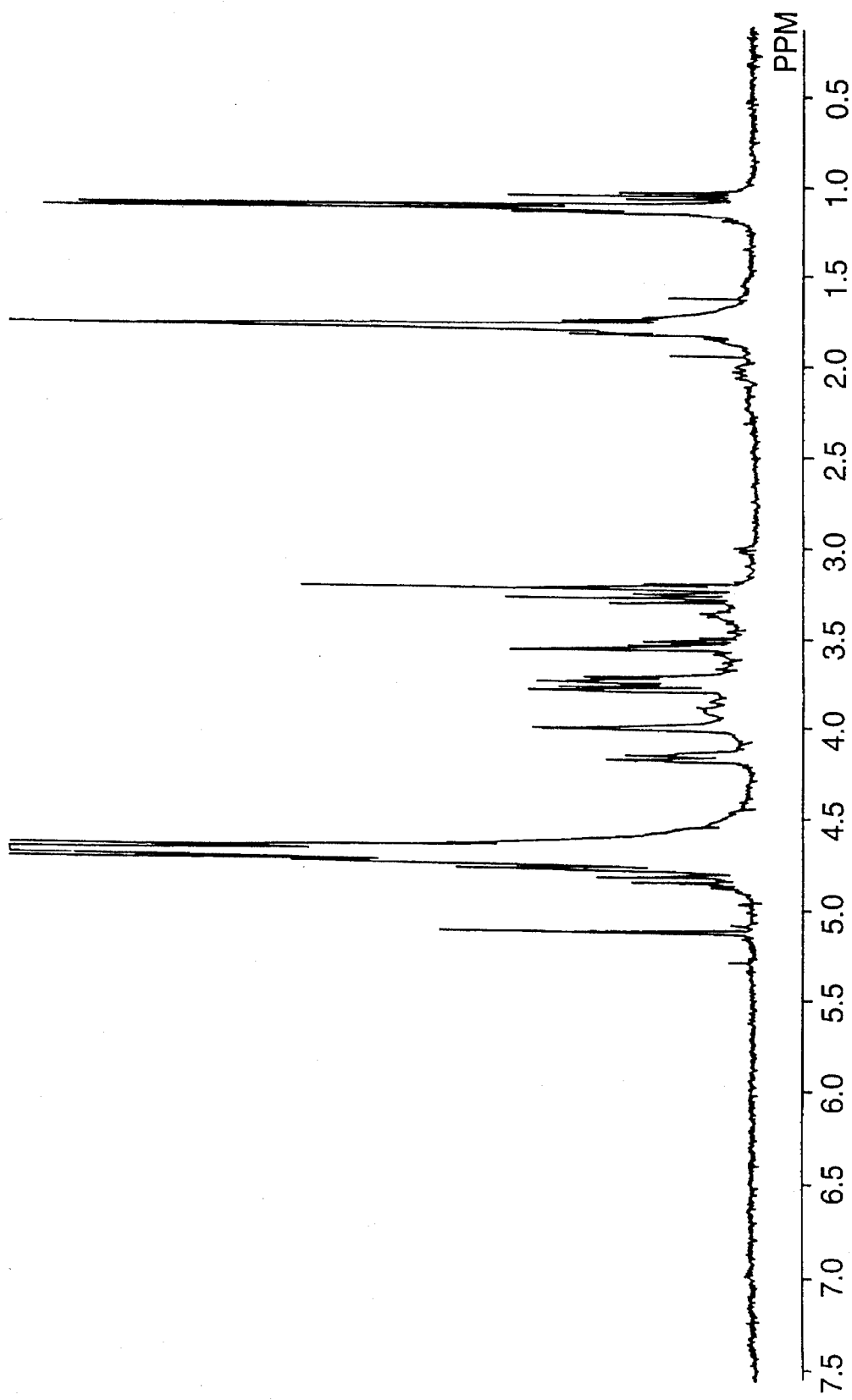
FIG. 22 shows $^1$H-NMR spectrum of compound (14).

2.9 mg of compound (13) obtained in Example 18 was dissolved in a combined solvent of 1 ml water and 1 ml methanol, and an aqueous 6-fold equivalent 1N sodium hydroxide solution was added thereto, and the mixture was allowed to react for 3 hours. The reaction solution was concentrated and then purified by HP-20 column chromatography, whereby compound (14), 2.6 mg, was obtained (yield: 98%). $^1$H-NMR spectrum (D$_2$O): see FIG. 22.

(Test Example 1)

Physiological activity of synthetic lepidimide and lepidimoide derivatives

Compounds (1), (8a), (9a), (10a), (12) +(12'), and (14) synthesized above were examined for growth promotion effect on *Amaranthus caudatus* L. hypocotyls in the same manner as in Example 1 (2) ①. *Amaranthus caudatus* L. seeds were placed on a filter paper imersed with 0.8 ml of a test solution (an aqueous solution of each compound synthesized as described above [$10^{-5}$ to $3 \times 10^{-4}$M]) in a Petri dish of 3 cm diameter and were then allowed to stand over 5 days at 25° C. in the dark, and the length of germinated hypocotyls was determined. The compound activities expressed in terms of hypocotyl length were compared.

The results are shown in Table 12.

TABLE 12

Comparison of physiological activities of synthetic lepidimoide and lepidimoide derivatives

| | Compond No. | | | | | |
|---|---|---|---|---|---|---|
| | 1· | 8a | 9a | 10a | 12 + 12' | 14 |
| Activity | ++++ | ++ | ++ | ++ | + | +++ |

++++: The same as that of natural lepidimoide
+++: 75% of the acivity of natural lepidimoide
++: 50% of the activity of natural lepidimoide
+: 25% of the activity of natural lepidimoide

We claim:

1. A process for the preparation of a compound represented by the formula:

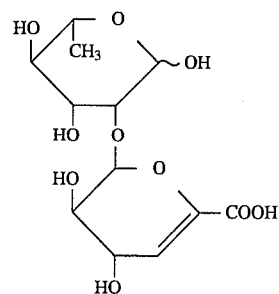

and salts thereof, which comprises chemical hydrolysis of a compound represented by the formula:

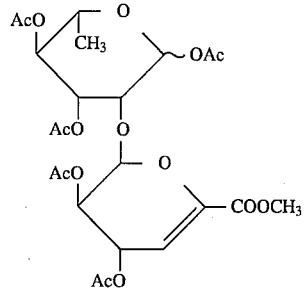

or salts thereof.

2. A process for the preparation of physiologically active substances of plant, which comprises immersing plant seeds in water and then collecting from the extract the compound represented by the formula:

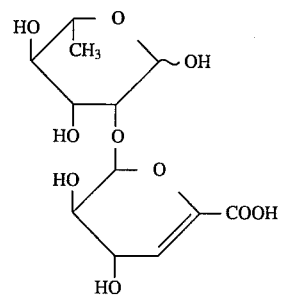

or a salt thereof, wherein the plant seeds are those of a plant selected from a group consisting of cress, sunflower, spinach, corn, okra, carrot, oat, parsley, barnyard grass, cayenne pepper, buckwheat, tomato, cabbage, lettuce, cockscomb, burdock, trefoil, pea, radish, and Persian speedwell.

* * * * *